United States Patent
Sampognaro et al.

(10) Patent No.: US 8,198,438 B2
(45) Date of Patent: Jun. 12, 2012

(54) PYRROLOTRIAZINE KINASE INHIBITORS

(75) Inventors: Anthony J. Sampognaro, Meriden, CT (US); Mark D. Wittman, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 293 days.

(21) Appl. No.: 12/596,058

(22) PCT Filed: Apr. 17, 2008

(86) PCT No.: PCT/US2008/060551
§ 371 (c)(1),
(2), (4) Date: Oct. 15, 2009

(87) PCT Pub. No.: WO2008/131050
PCT Pub. Date: Oct. 30, 2008

(65) Prior Publication Data
US 2010/0113454 A1 May 6, 2010

Related U.S. Application Data

(60) Provisional application No. 60/912,446, filed on Apr. 18, 2007.

(51) Int. Cl.
C07D 487/04 (2006.01)
A61K 31/53 (2006.01)
A61K 35/00 (2006.01)

(52) U.S. Cl. ........................ 544/183; 514/243

(58) Field of Classification Search .......... 544/183; 514/243
See application file for complete search history.

(56) References Cited

U.S. PATENT DOCUMENTS

| | | | |
|---|---|---|---|
| 6,670,357 B2 | 12/2003 | Leftheris et al. | |
| 6,869,952 B2 | 3/2005 | Bhide et al. | |
| 6,982,265 B1 | 1/2006 | Hunt et al. | |
| 7,531,539 B2 * | 5/2009 | Fink et al. | 514/243 |
| 7,534,792 B2 * | 5/2009 | Wittman et al. | 514/243 |
| 7,713,973 B2 * | 5/2010 | Dong et al. | 514/243 |
| 7,879,855 B2 * | 2/2011 | Wittman et al. | 514/243 |
| 2004/0157846 A1 | 8/2004 | Chen et al. | |
| 2006/0084650 A1 | 4/2006 | Dong et al. | |

FOREIGN PATENT DOCUMENTS

| | | |
|---|---|---|
| WO | WO 00/71129 | 11/2000 |
| WO | WO 2004/087056 | 10/2004 |
| WO | WO 2006/035061 | 4/2006 |
| WO | WO 2006/044687 | 4/2006 |

OTHER PUBLICATIONS

Cohen et al., Current Opinion in Chemical Biology, 3,459-465, 1999.*
Freshney et al., Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141 802-810, 1999.*
Golub et al., Science, 286, 531-537, 1999.*
Cecil Textbook of Medicine, 20th Edition, vol. 1, pp. 1004-1010 (1996).
Malumbres et al., Trends in Biochemical Sciences, vol. 30(11), pp. 630-641 (2005).
Lolli et al., Cell Cycle, vol. 4(4), pp. 572-577 (2005).
Sherr et al., Genes & Developement, vol. 18, pp. 2699-2711 (2004).
Fischer, Cell Cycle, vol. 3(6), pp. 742-746 (2004).
Blain et al., The Journal of Biological Chemistry, vol. 272(41), pp. 25863-25872 (1997).
LuValle et al., Frontiers in Bioscience, vol. 5, d493-503 (2000).
Patel et al., Biochem. Soc. Trans., vol. 32(5), pp. 803-808 (2004).
Jope et al., Trends in Biochemical Sciences, vol. 29(2), pp. 95-102 (2004).
Mass, R. D., Int. Radiation Oncology Bio. Phys., vol. 58(3), pp. 932-940 (2001).
Fabbro et al., Pharmacology & Therapeutics, vol. 93, pp. 79-98 (2002).

* cited by examiner

*Primary Examiner* — Venkataraman Balasubramanian
(74) *Attorney, Agent, or Firm* — Elliott Korsen

(57) ABSTRACT

The invention provides compounds of formula I

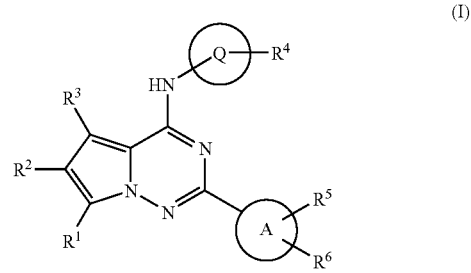

and pharmaceutically acceptable salts thereof.
The formula I compounds inhibit tyrosine kinase activity thereby making them useful as anti-cancer agents and for the treatment of Alzheimer's Disease.

9 Claims, No Drawings

PYRROLOTRIAZINE KINASE INHIBITORS

FIELD OF THE INVENTION

The invention relates to novel pyrrolotriazine compounds that are useful as inhibitors of tyrosine kinases. This invention also relates to pharmaceutical compositions containing the compounds and methods of using the compounds for the treatment of proliferative and other diseases, in particular, certain types of cancer.

BACKGROUND

The invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, Alzheimer's disease, angiogenic diseases and immunologic disorders (Powis, G.; Workman P. Signaling Targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Tyrosine kinases play a critical role in signal transduction for several cellular functions including cell proliferation, carcinogenesis, apoptosis, and cell differentiation Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes.

It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and (h) factors that improve manufacturing costs or feasibility.

SUMMARY OF THE INVENTION

The invention provides compounds of Formula I, including stereoisomers, tautomers and pharmaceutically acceptable salts thereof, which are useful as inhibitors of tyrosine kinase enzymes.

The invention also provides pharmaceutical compositions comprising a pharmaceutically acceptable carrier and one or more of the compounds of the present invention or a stereoisomer, tautomer or pharmaceutically acceptable salt thereof.

The invention also provides a method for treating a condition associated with one or more tyrosine kinase inhibitors comprising administering to a patient in need of such treatment, a therapeutically effective amount of a compound of formula I or a stereoisomer, tautomer or pharmaceutically acceptable salt thereof, and optionally one or more other anticancer agent or treatment.

The invention also provides methods for treating cancer using the compounds of the invention or a stereoisomer, tautomer or pharmaceutically acceptable salt thereof.

The invention also provides the compounds of the present invention or a stereoisomer, tautomer or pharmaceutically acceptable salt thereof, for use in therapy.

The present invention also provides the use of the compounds of the present invention or a stereoisomer, tautomer or pharmaceutically acceptable salt thereof, for the manufacture of a medicament for the treatment of a proliferative disease such as cancer.

These and other features of the invention will be set forth in the expanded form as the disclosure continues.

DETAILED DESCRIPTION OF THE INVENTION

The invention provides for compounds of formula I, pharmaceutical compositions employing such compounds and for methods of using such compounds.

In accordance with the invention, there are disclosed compounds of formula I

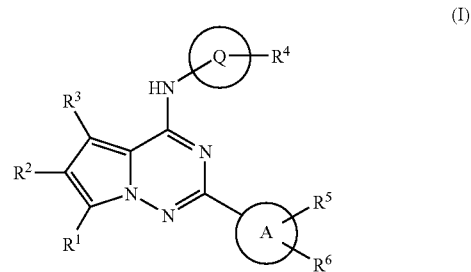

wherein:

Q is aryl, substituted aryl, heteroaryl or substituted heteroaryl;

A is alkyl, substituted alkyl, cycloalkyl, substituted cycloalkyl, cycloalkenyl, substituted cycloalkenyl, aryl, substituted aryl, heterocyclyl, substituted heterocyclyl, heteroaryl, or substituted heteroaryl;

$R^1$, $R^2$, and $R^3$ are independently hydrogen, alkyl, substituted alkyl, cycloalkyl, substituted cycloalkyl, hydroxy, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl or alkylcarbonyl;

$R^4$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heterolakenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

R⁵ is hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl, —COalkyl, —CO substituted alkyl; —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —NHCOalkyl, —NHCO substituted alkyl; —NHCO aryl, —NHCO substituted aryl, —NHCO heteroaryl, —NHCO substituted heteroaryl, —NHCO heterocyclyl, —NHCO substituted heterocyclyl, —SO₂ alkyl, —SO₂ substituted alkyl; —SO₂ aryl, —SO₂ substituted aryl, —SO₂ heteroaryl, —SO₂ substituted heteroaryl, —SO₂ heterocyclyl or —SO₂ substituted heterocyclyl;

R⁶ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

In another embodiment of the invention, there are disclosed compounds of formula I

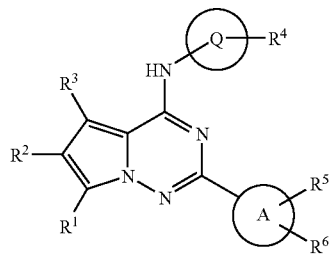

wherein:

Q is heteroaryl or substituted heteroaryl;

A is alkyl, substituted alkyl, cycloalkyl, substituted cycloalkyl, cycloalkenyl, substituted cycloalkenyl, heterocyclyl or substituted heterocyclyl;

R¹, R², and R³ are independently hydrogen, alkyl, substituted alkyl, cycloalkyl, substituted cycloalkyl, hydroxy, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl or alkylcarbonyl;

R⁴ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heterolakenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

R⁵ is hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl, —COalkyl, —CO substituted alkyl, —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO$_2$ alkyl, —SO$_2$ substituted alkyl; —SO$_2$ aryl, —SO$_2$ substituted aryl, —SO$_2$ heteroaryl, —SO$_2$ substituted heteroaryl, —SO$_2$ heterocyclyl or —SO$_2$ substituted heterocyclyl;

R$^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

In a further embodiment of the invention, there are disclosed compounds of formula II

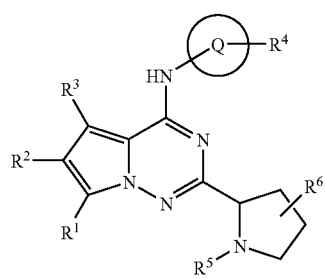

(II)

wherein:
Q is pyrazole or imidazole;
R$^1$, R$^2$, and R$^3$ are independently hydrogen, alkyl, substituted alkyl or halogen;
R$^4$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heterolakenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

R$^5$ is hydrogen, alkyl, substituted alkyl, alkylidene, substituted alkylidene, haloalkyl, arylalkyl, alkanoyl, substituted alkanoyl, aminoalkyl, substituted aminoalkyl, hydroxyalkyl, amide, substituted amide, carbamate, substituted carbamate, ureido, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, thioalkyl, alkylsulfonyl, alkylsulfinyl, carboxy, alkoxycarbonyl, carbamoyl, alkenyl, substituted alkenyl, alkynyl, substituted alkynyl, aryl, substituted aryl, heteroaryl, substituted heteroaryl, arylheteroaryl, arylalkoxycarbonyl, heteroarylalkyl, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylsulfonyl, arylalkylsulfonyl, alkylsulfonyl, or alkylaminocarbonyl, —COalkyl, —CO substituted alkyl; —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO$_2$ alkyl, —SO$_2$ substituted alkyl; —SO$_2$ aryl, —SO$_2$ substituted aryl, —SO$_2$ heteroaryl, —SO$_2$ substituted heteroaryl, —SO$_2$ heterocyclyl or —SO$_2$ substituted heterocyclyl;

R$^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

In a further embodiment of the invention, there are disclosed compounds of formula III

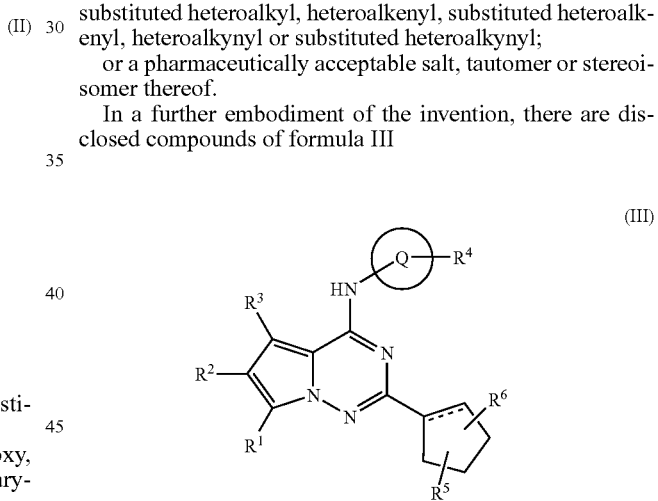

(III)

wherein:
Q is pyrazole or imidazole;
R$^1$, R$^2$, and R$^3$ are independently the group consisting of hydrogen, alkyl, substituted alkyl or halogen;
R$^4$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^5$ is hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl, —COalkyl, —CO substituted alkyl, —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO$_2$ alkyl, —SO$_2$ substituted alkyl; —SO$_2$ aryl, —SO$_2$ substituted aryl, —SO$_2$ heteroaryl, —SO$_2$ substituted heteroaryl, —SO$_2$ heterocyclyl or —SO$_2$ substituted heterocyclyl;

$R^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

In another embodiment of the invention, there are disclosed compounds of formula IV

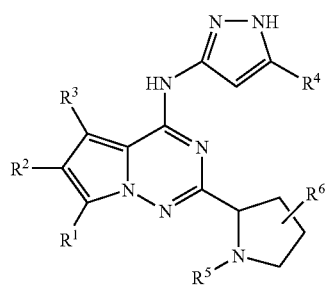

(IV)

wherein:
$R^1$, $R^2$, and $R^3$ are independently hydrogen, alkyl, substituted alkyl or halogen;
$R^4$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

$R^5$ is hydrogen, alkyl, substituted alkyl, alkylidene, substituted alkylidene, haloalkyl, arylalkyl, alkanoyl, substituted alkanoyl, aminoalkyl, substituted aminoalkyl, hydroxyalkyl, amide, substituted amide, carbamate, substituted carbamate, ureido, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, thioalkyl, alkylsulfonyl, alkylsulfinyl, carboxy, alkoxycarbonyl, carbamoyl, alkenyl, substituted alkenyl, alkynyl, substituted alkynyl, aryl, substituted aryl, heteroaryl, substituted heteroaryl, arylheteroaryl, arylalkoxycarbonyl, heteroarylalkyl, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylsulfonyl, arylalkylsulfonyl, alkylsulfonyl, or alkylaminocarbonyl, —COalkyl, —CO substituted alkyl; —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO$_2$ alkyl, —SO$_2$ substituted alkyl; —SO$_2$ aryl, —SO$_2$ substituted aryl, —SO$_2$ heteroaryl, —SO$_2$ substituted heteroaryl, —SO$_2$ heterocyclyl or —SO$_2$ substituted heterocyclyl;

$R^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

In another embodiment of the invention, there are disclosed compounds of formula V

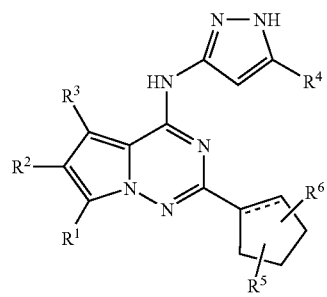

(V)

wherein:

R¹, R², and R³ are independently hydrogen, alkyl, substituted alkyl or halogen;

R⁴ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heterolakenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

R⁵ is hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl, —COalkyl, —CO substituted alkyl, —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO₂ alkyl, —SO₂ substituted alkyl; —SO₂ aryl, —SO₂ substituted aryl, —SO₂ heteroaryl, —SO₂ substituted heteroaryl, —SO₂ heterocyclyl or —SO₂ substituted heterocyclyl;

R⁶ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

Compounds of the invention include
(S)-(2-(4-(5-cyclopropyl-1H-pyrazol-3-ylamino)pyrrolo[1,2-f][1,2,4]triazin-2-yl)pyrrolidin-1-yl)(6-fluoropyridin-3-yl)methanone;
(S)-(2-(4-(5-Cyclopropyl-1H-pyrazol-3-ylamino)pyrrolo[1,2-f][1,2,4]triazin-2-yl)pyrrolidin-1-yl)(thiazol-2-yl)methanone;
(S)-(2-(4-(5-Cyclopropyl-1H-pyrazol-3-ylamino)pyrrolo[1,2-f][1,2,4]triazin-2-yl)pyrrolidin-1-yl)(pyrazin-2-yl)methanone;
(S)-tert-Butyl 4-(2-(4-(5-cyclopropyl-1H-pyrazol-3-ylamino)pyrrolo[1,2-f][1,2,4]triazin-2-yl)pyrrolidine-1-carbonyl)piperidine-1-carboxylate;
(S)-(2-(4-(5-cyclopropyl-1H-pyrazol-3-ylamino)pyrrolo[1,2-f][1,2,4]triazin-2-yl)pyrrolidin-1-yl)(piperidin-4-yl)methanone;
(S)-(2-(4-(5-Cyclopropyl-1H-pyrazol-3-ylamino)pyrrolo[1,2-f][1,2,4]triazin-2-yl)pyrrolidin-1-yl)(pyridin-3-yl)methanone;
(S)-(2-(4-(5-Cyclopropyl-1H-pyrazol-3-ylamino)pyrrolo[1,2-f][1,2,4]triazin-2-yl)pyrrolidin-1-yl)(1H-pyrazol-3-yl)methanone;
(S)-5-(4-(5-Cyclopropyl-1H-pyrazol-3-ylamino)pyrrolo[1,2-f][1,2,4]triazin-2-yl)-1-(6-fluoronicotinoyl)pyrrolidin-2-one;
(R)-Benzyl 2-(4-oxo-3,4-dihydropyrrolo[1,2-f][1,2,4]triazin-2-yl)pyrrolidine-1-carboxylate;
(R)-(2-(4-(5-Cyclopropyl-1H-pyrazol-3-ylamino)pyrrolo[1,2-f][1,2,4]triazin-2-yl)pyrrolidin-1-yl)(pyrazin-2-yl)methanone;
(R)-(2-(4-(5-Cyclopropyl-1H-pyrazol-3-ylamino)pyrrolo[1,2-f][1,2,4]triazin-2-yl)pyrrolidin-1-yl)(piperidin-4-yl)methanone;
(R)-(2-(4-(5-Cyclopropyl-1H-pyrazol-3-ylamino)pyrrolo[1,2-f][1,2,4]triazin-2-yl)pyrrolidin-1-yl)(thiazol-2-yl)methanone;
(R)-2-(4-(5-Cyclopropyl-1H-pyrazol-3-ylamino)pyrrolo[1,2-f][1,2,4]triazin-2-yl)-N-(6-fluoropyridin-3-yl)pyrrolidine-1-carboxamide;
2-(4-(5-Cyclopropyl-1H-pyrazol-3-ylamino)pyrrolo[1,2-f][1,2,4]triazin-2-yl)-N-(6-fluoropyridin-3-yl)cyclopent-1-enecarboxamide; and
2-(4-(5-Cyclopropyl-1H-pyrazol-3-ylamino)pyrrolo[1,2-f][1,2,4]triazin-2-yl)-N-(pyrazin-2-yl)cyclopent-1-enecarboxamide.

In another embodiment the present invention provides a pharmaceutical composition comprising a pharmaceutically acceptable carrier and one or more of the compounds of the present invention or a stereoisomer, tautomer or pharmaceutically acceptable salt thereof.

In another embodiment the present invention provides a pharmaceutical composition comprising a pharmaceutically acceptable carrier and a therapeutically effective amount of one or more of the compounds of the present invention or a stereoisomer, tautomer or pharmaceutically acceptable salt thereof.

In another embodiment the present invention provides a method for treating protein kinase related disorders comprising administering to a patient in need of such treatment a therapeutically effective amount of one or more of the compounds of the present invention or a stereoisomer, tautomer or pharmaceutically acceptable salt thereof.

In another embodiment the present invention provides a method for treating tyrosine kinase related disorders comprising administering to a patient in need of such treatment a therapeutically effective amount of one or more of the compounds of the present invention or a stereoisomer, tautomer or pharmaceutically acceptable salt thereof.

In another embodiment, the protein kinase related disorder is selected from the group consisting of cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

In another embodiment, the present invention provides a method of treating a patient in need of protein kinase related disorder treatment, comprising administering a compound of the present invention or a stereoisomer, tautomer or pharmaceutically acceptable salt thereof in an amount effective to treat a protein kinase related disorder.

In another embodiment, the present invention provides a pharmaceutical composition further comprising one or more additional anticancer agent or treatment, such as radiation therapy.

In another embodiment, the present invention provides a compound of the present invention for use in therapy.

In another embodiment, the present invention provides a compound of the present invention for use in therapy for treating a protein kinase related disorder.

In another embodiment, the present invention provides a compound of the present invention for use in therapy for treating a tyrosine kinase related disorder.

In another embodiment, the present invention also provides the use of a compound of the present invention for the manufacture of a medicament for the treatment of a protein kinase related disorder.

In another embodiment, the present invention also provides the use of a compound of the present invention for the manufacture of a medicament for the treatment of a tyrosine kinase related disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a protein kinase related disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

The following are definitions of terms that may be used in the specification. The initial definition provided for a group or term herein applies to that group or term throughout the specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" or "alkylene" refers to both branched and straight-chain saturated aliphatic hydrocarbon groups of 1 to 20 carbon atoms, preferably 1 to 7 carbon atoms. The expression "lower alkyl" refers to unsubstituted alkyl groups of 1 to 4 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where it is noted above that the substituent is further substituted, it will be with alkyl, alkoxy, aryl or arylalkyl.

The term "alkenyl" or "alkenylene" refers to hydrocarbon chains of either a straight or branched configuration having the specified number of carbon atoms and one or more unsaturated carbon-carbon bonds which may occur in any stable point along the chain. These may be groups of 2 to 20 carbon atoms, preferably 2 to 15 carbon atoms, and most preferably 2 to 8 carbon atoms, having one to four double bonds. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" or "alkynylene" refers to hydrocarbon chains of either a straight or branched configuration and one or more carbon-carbon triple bonds which may occur in any stable point along the chain. These may include groups of 2 to 20 carbon atoms, preferably 2 to 15 carbon atoms, and most preferably 2 to 8 carbon atoms, having one to four triple bonds. Examples of alkynyl include, but are not limited to s ethynyl, propynyl, butynyl, pentynyl, hexynyl and the like.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The term "alkoxy" or "alkyloxy" refers to an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

The term "halogen" or "halo" refers to fluorine, chlorine, bromine and iodine.

The term "haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "carbocyclic ring" or "carbocyclyl" refers to stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl. When the term "carbocycle" is used, it is intended to include "aryl".

The term "bicyclic carbocycle" or "bicyclic carbocyclic group" refers to a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like.

Exemplary substituents include one or more alkyl or arylalkyl groups as described above or one or more groups described above as alkyl substituents.

The terms "heterocycle", "heterocyclic" and "heterocyclyl" refer to an optionally substituted, saturated, partially unsaturated or fully unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized to —NO—, —SO—, or —$SO_2$— and the nitrogen heteroatoms may also optionally be quaternized. The heterocyclic group may be attached at any heteroatom or carbon atom. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "heteroatoms" shall include oxygen, sulfur and nitrogen.

The term "alkylsulfone" refers to —$R^kS(=O)_2R^k$, wherein $R^k$ is an alkyl or substituted alkyl.

The term "oxo" refers to the divalent radical =O.

The term "carbamate" refers to the group —$OC(=O)NH_2$.

The term "amide" refers to the group —$C(=O)NH_2$.

The term "sulfonamide" refers to the group —$SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —$C(=O)NR^mR^n$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group —$SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group —$OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group —$NHC(=O)NH_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —$N(O)_2$.

The term "thio" refers to the group —SH.

The term "alkylthio" refers to the group —$SR^s$ where $R^s$ is an alkyl, substituted alkyl, cycloalkyl, or substituted cycloalkyl.

The term "thioalkyl" refers to the group —$R^tS$ where $R^t$ is an alkyl, substituted alkyl, cycloalkyl, or substituted cycloalkyl.

The term "alkylsulfonyl" refers to the group —$S(=O)R^u$ where $R^u$ is an alkyl, substituted alkyl, cycloalkyl, or substituted cycloalkyl.

The term "alkylsulfinyl" refers to the group —$S(=O)R^v$ where $R^v$ is an alkyl, substituted alkyl, cycloalkyl, or substituted cycloalkyl.

The term "carboxy" refers to the group —$C(=O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —$C(=O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —$OC(=O)R^x$, where $R^x$ is an alkyl or substituted alkyl, or an aryl or substituted aryl, respectively.

The term "carbamoyl" refers to the groups —$OC(=O)NH_2$, —$OC(=O)NHR^x$, and/or —$OC(=O)NR^yR^z$, wherein $R^y$ and $R^z$ are independently selected from alkyl and substituted alkyl.

The group —$NR^6(C=O)R^9$ refers to a group where $R^6$ is selected from hydrogen, lower alkyl and substituted lower alkyl, and $R^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a $C(=O)$.

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed according to methods known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the invention may be delivered in prodrug form. Thus, the invention is intended to cover prodrugs of the claimed compounds, methods of delivering the same and compositions containing the same. "Prodrugs" are intended to include any covalently bonded carriers that release an active parent drug of the invention in vivo when such prodrug is administered to a mammalian subject. Prodrugs of the invention are prepared by modifying functional groups present in the compound in such a way that the modifications are cleaved, either in routine manipulation or in vivo, to the parent compound. Prodrugs include compounds of the invention wherein a hydroxy, amino, or sulfhydryl group is bonded to any group that, when the prodrug of the invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the invention.

Various forms of prodrugs are well known in the art. For examples of such prodrug derivatives, see:
a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);
b) *A Textbook of Drug Design and Development*, edited by Krosgaard-Larsen and H. Bundgaard, Chapter 5, "Design and Application of Prodrugs," by H. Bundgaard, at pp. 113-191 (1991);
c) H. Bundgaard, *Advanced Drug Delivery Reviews*, Vol. 8, p. 1-38 (1992);
d) H. Bundgaard, et al., *Journal of Pharmaceutical Sciences*, Vol. 77, p. 285 (1988); and
e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice*, ed. F. D. King, The Royal Society of Chemistry, Cambridge, UK, 1994, which is incorporated herein by reference in its entirety.

It should further be understood that solvates (e.g., hydrates) of the compounds of formula I are also with the scope of the invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that these recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The invention further includes compositions comprising one or more compounds of the invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Utility

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

Further, another aspect of the invention provides for the use of a compound of formula I or a pharmaceutically acceptable salt thereof in the manufacture of a medicament for use in the treatment of certain types of cancer including cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecule compounds such as ZD6474 and SU6668; Vatalanib, Nexavar® (Sorafenib tosylate), Sutent® (sunitinib malate), CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; protein tyrosine kinase inhibitors such as, e.g. Gleevec® (imatinib mesylate) and dasatinib Sprycel® (dasatinib), Casodex® (bicalutamide), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists, e.g., 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medullobalstoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anti-cancer or cytotoxic agents when a combination formulation is inappropriate. The invention is not limited in the sequence of administration; compounds of formula I may be administered either prior to or after administration of the known anti-cancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

A. CDK 2/Cyclin E Kinase Assay

The assays were performed in U-bottom 384-well plates. The final assay volume was 30 µl prepared from 15 µl additions of enzyme and substrates (fluoresceinated CDK2E substrate peptide and ATP) and test compounds in assay buffer (100 mM HEPES pH 7.4, 10 mM MgCl$_2$, 0.015% Brij35 and 4 mM DTT). The reaction was initiated by the combination of bacterially expressed, CDK2E with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 30 µM; FL-peptide, 1.5 µM; CDK2E, 0.2 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

B. FLT3

The assays were performed in U-bottom 384-well plates. The final assay volume was 30 µl prepared from 15 µl additions of enzyme and substrates (fluoresceinated FLT3 substrate peptide and ATP) and test compounds in assay buffer (100 mM HEPES pH 7.4, 10 mM MgCl$_2$, 0.015% Brij35 and 4 mM DTT). The reaction was initiated by the combination of FLT3 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 200 µM, FL-peptide, 1.5 µM; FLT3, 4.5 nM and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. $IC_{50}$ values were derived by non-linear regression analysis.

C. GSK3-β

The assays were performed in U-bottom 384-well plates. The final assay volume was 30 μl prepared from 15 μl additions of enzyme and substrates (fluoresceinated peptide FL-GSK substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of GSK3-β with substrates and test compounds. The reaction was incubated at room temperature for 60 min. and terminated by adding 30 μl of 35 mM EDTA to each sample. The reaction mixture was analyzed on the Caliper LabChip 3000 (Caliper, Hopkinton, Mass.) by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 30 μM; FL-GSK substrate, 1.5 μM; His-GSK3B, 2.4 nM; and DMSO, 1.6%.

D. IGF1-Receptor Tyrosine Kinase Assay

The assays were performed in U-bottom 384-well plates. The final assay volume was 30 μl prepared from 15 μl additions of enzyme and substrates (fluoresceinated IGF1R substrate peptide and ATP) and test compounds in assay buffer (100 mM HEPES pH 7.4, 10 mM $MnCl_2$, 0.015% Brij35 and 4 mM DTT). The reaction was initiated by the combination of IGF1-receptor with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 μM; FL-peptide, 1.5 μM; IGF1-Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis E. Insulin Receptor Tyrosine Kinase Assay The assays were performed in U-bottom 384-well plates. The final assay volume was 30 μl prepared from 15 μl additions of enzyme and substrates (fluoresceinated InsR substrate peptide and ATP) and test compounds in assay buffer (100 mM HEPES pH 7.4, 10 mM $MnCl_2$, 0.015% Brij35 and 4 mM DTT). The reaction was initiated by the combination of Insulin Receptor with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 μM; FL-peptide, 1.5 μM; Insulin Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis

F. JAK2

The assays were performed in U-bottom 384-well plates. The final assay volume was 30 μl prepared from 15 μl additions of enzyme and substrates (fluoresceinated peptide FL-JAK2 substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of activated JAK2 with substrates and test compounds. The reaction was incubated at room temperature for 60 min. and terminated by adding 30 μl of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 μM; FL-JAK2 peptide, 1.5 μM; His-CDK5/p25, 2.6 nM; and DMSO, 1.6%.

G. LCK Kinase Assay

The assays were performed in U-bottom 384-well plates. The final assay volume was 30 μl prepared from 15 μl additions of enzyme and substrates (fluoresceinated LCK substrate peptide and ATP) and test compounds in assay buffer (100 mM HEPES pH 7.4, 10 mM $MnCl_2$, 0.015% Brij35 and 4 mM DTT). The reaction was initiated by the combination of LCK with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 3 μM; FL-peptide, 1.5 μM; Lck, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

H. MapKapK2

The assays were performed in U-bottom 384-well plates. The final assay volume was 30 μl prepared from 15 μl additions of enzyme and substrates (fluoresceinated MK2 substrate peptide and ATP) and test compounds in assay buffer (100 mM HEPES pH 7.4, 10 mM $MgCl_2$, 0.015% Brij35 and 4 mM DTT). The reaction was initiated by the combination of MapKapK2 with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 1 μM; FL-peptide, 1.5 μM; MapKapK2, 0.08 nM; Brij35, 0.015% and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

I. Met Kinase Assay

Kinase reactions consisted of 0.75 ng of baculovirus expressed GST-Met, 3 ug poly(Glu/Tyr) (Sigma), 0.12 µCi 33P γ-ATP, 1 µM ATP in 30 µl kinase buffer (20 mm TRIS-C1, 5 mM MnCl$_2$, 0.1 mg/ml BSA, 0.5 mM DTT). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity (IC$_{50}$). Compounds were dissolved at 10 mM in dimethylsulfoxide (DMSO) and evaluated at seven concentrations, each in triplicate.

J. p38alpha Assay

The assays were performed in U-bottom 384-well plates. The final assay volume was 30 µl prepared from 15 µl additions of enzyme and substrates (fluoresceinated P38a substrate peptide and ATP) and test compounds in assay buffer (100 mM HEPES pH 7.2, 10 mM MgCl$_2$, 0.015% Brij35 and 4 mM DTT). The reaction was initiated by the combination of activated p38alpha with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38alpha, 6 nM; and DMSO, 1.6%.

K. p38beta Assay

The assays were performed in U-bottom 384-well plates. The final assay volume was 30 µl prepared from 15 µl additions of enzyme and substrates (fluoresceinated P38b substrate peptide and ATP) and test compounds in assay buffer (100 mM HEPES pH 7.2, 10 mM MgCl$_2$, 0.015% Brij35 and 4 mM DTT). The reaction was initiated by the combination of activated p38beta with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38beta, 1 nM; and DMSO, 1.6%.

L. Protein Kinase A

The assays were performed in U-bottom 384-well plates. The final assay volume was 30 µl prepared from 15 µl additions of enzyme and substrates (fluoresceinated PKA substrate peptide and ATP) and test compounds in assay buffer (100 mM HEPES pH 7.4, 10 mM MgCl$_2$, 0.015% Brij35 and 4 mM DTT). The reaction was initiated by the combination of Protein kinase A with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM, Protein kinase A 1 nM, and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

M. Protein Kinase C-alpha

The assays were performed in U-bottom 384-well plates. The final assay volume was 30 µl prepared from 15 µl additions of enzyme and substrates (fluoresceinated PKCa substrate peptide and ATP) and test compounds in assay buffer (100 mM HEPES pH 7.4, 10 mM MgCl$_2$, 0.015% Brij35 and 4 mM DTT). The reaction was initiated by the combination of Protein kinase C-alpha with lipids, substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 1 µM; FL-peptide, 1.5 µM; Protein kinase C-alpha, 1 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

N. TrkA Kinase Assay

Kinase reactions consisted of 0.12 ng of baculovirus expressed His-TrkA, 3 ug poly(Glu/Tyr) (Sigma), 0.24 µCi 33P γ-ATP, 30 µM ATP in 30 µl kinase buffer (20 mm MOPS, 10 mM MgCl$_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity (IC$_{50}$). Compounds were dissolved at 10 mM in dimethylsulfoxide (DMSO) and evaluated at seven concentrations, each in triplicate.

O. TrkB Kinase Assay

Kinase reactions consisted of 0.75 ng of baculovirus expressed His-TrkB, 3 ug poly(Glu/Tyr) (Sigma), 0.24 µCi 33P γ-ATP, 30 µM ATP in 30 µl kinase buffer (20 mm MOPS, 10 mM MgCl$_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity (IC$_{50}$). Compounds were dissolved at 10 mM in dimethylsulfoxide (DMSO) and evaluated at seven concentrations, each in triplicate.

The instant compounds inhibit at least three of the following kinases: CDK2, Flt-3, GSK-3β, IGF1R, IR, JAK2, Met, Lck with IC$_{50}$ values <5 µM. Preferred compounds have IC$_{50}$ values between 0.001 and 1 µM. Compounds described herein were tested in the following assays. The following results were obtained.

| Example | CDK2E IC50 uM | Flt3 IC50 uM | GSK-3β IC50 uM | IGF1R IC50 uM | Jak2 IC50 uM | Met IC50 uM |
|---|---|---|---|---|---|---|
| 1 | 1.870 | 0.029 | 0.290 | 0.007 | | 0.028 |
| 2 | 0.088 | 0.001 | 0.024 | 0.005 | | 0.170 |
| 4 | 0.005 | 0.001 | 0.020 | 0.135 | | 1.779 |
| 6 | 0.615 | 0.097 | 0.092 | 4.055 | 10.680 | 10.460 |
| 7 | 0.054 | 0.004 | 0.051 | 0.068 | 0.036 | 1.167 |
| 12 | 0.256 | 0.006 | 0.003 | 4.934 | 4.478 | 10.820 |
| 13 | 17.420 | 0.308 | 4.453 | 0.314 | 22.020 | 50.000 |
| 15 | 0.162 | 0.024 | 0.011 | 2.518 | 0.324 | 6.33 |

Methods of Preparation

In general, the compounds of Formula (I) can be prepared in accordance with Scheme I and the general knowledge of one skilled in the art. Tautomers and solvates (e.g., hydrates) of the compounds of Formula (I) are also within the scope of the invention. Methods of solvation are generally known in the art. Accordingly, the compounds of the instant invention can be in the free or hydrate form, and can be obtained by methods exemplified in the following Schemes.

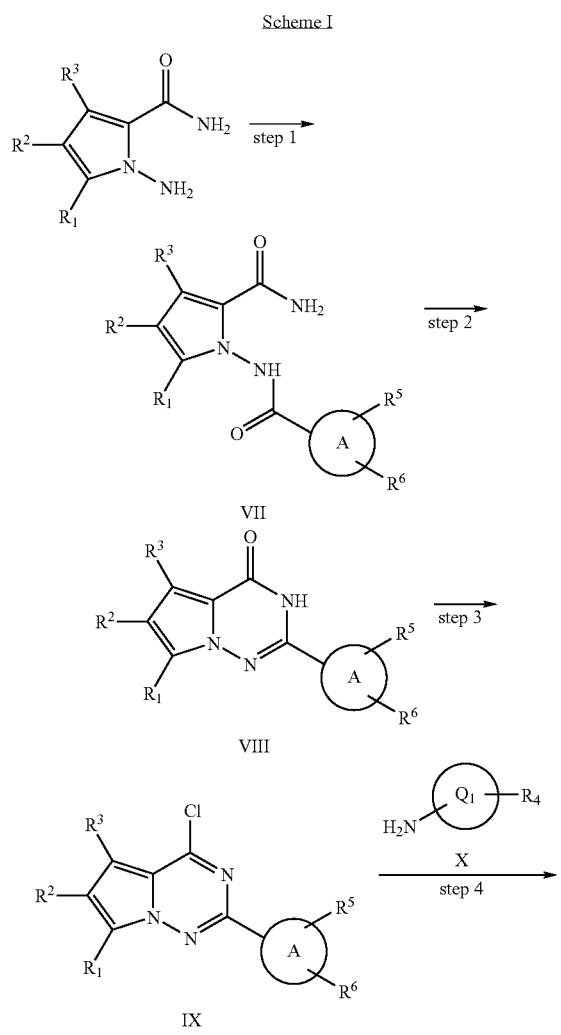

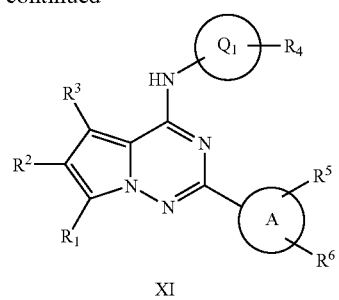

Step 1

Compound VII can be prepared by heating a mixture of the appropriately substituted 1-amino-1H-pyrrole-2-carboxamide with a cycloalkyl, substituted cycloalkyl, cycloalkenyl, substituted cycloalkenyl, aryl, substituted aryl, cycloheteroalkyl, substituted cycloheteroalkyl, heteroaryl, or substituted heteroaryl acid or anhydride using any number of dehydrating agents such as DCC, EDCI, or preferably EDAC in THF resulting in the acylated derivative.

Step 2

The resulting acyl derivative VII can be cyclized to compound VIII using any number of dehydrating agents, most preferably aqueous KOH or phosphorous oxychloride to provide the pyrrolotriazine-4-one, VIII.

Step 3

Pyrrolotriazine-4-one VIII can then be treated with a halogenating agent, such as, for example, phosphorus oxychloride (X=Cl) or phosphorus oxybromide (X=Br), optionally in the presence of a base, such as for example, diisopropylethylamine, to give compound IX.

Step 4

Compound IX of Scheme I is converted to compound XI by reaction with an appropriately substituted amino substituted aryl, heteroaryl or substituted heteroaryl derivative X in the presence of a base, such as, for example, diisopropylethylamine in a solvent, such as, for example, 1-methyl-2-pyrrolidinone (NMP).

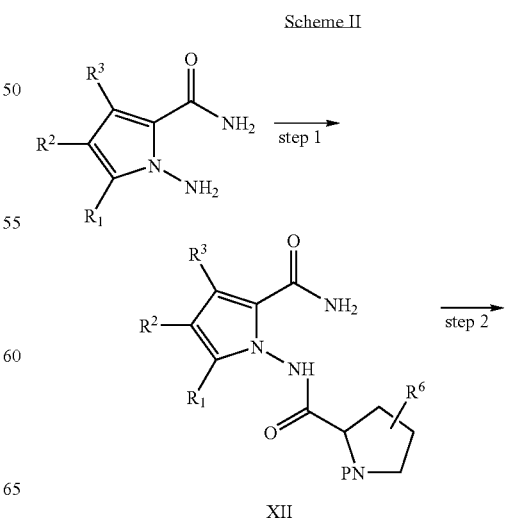

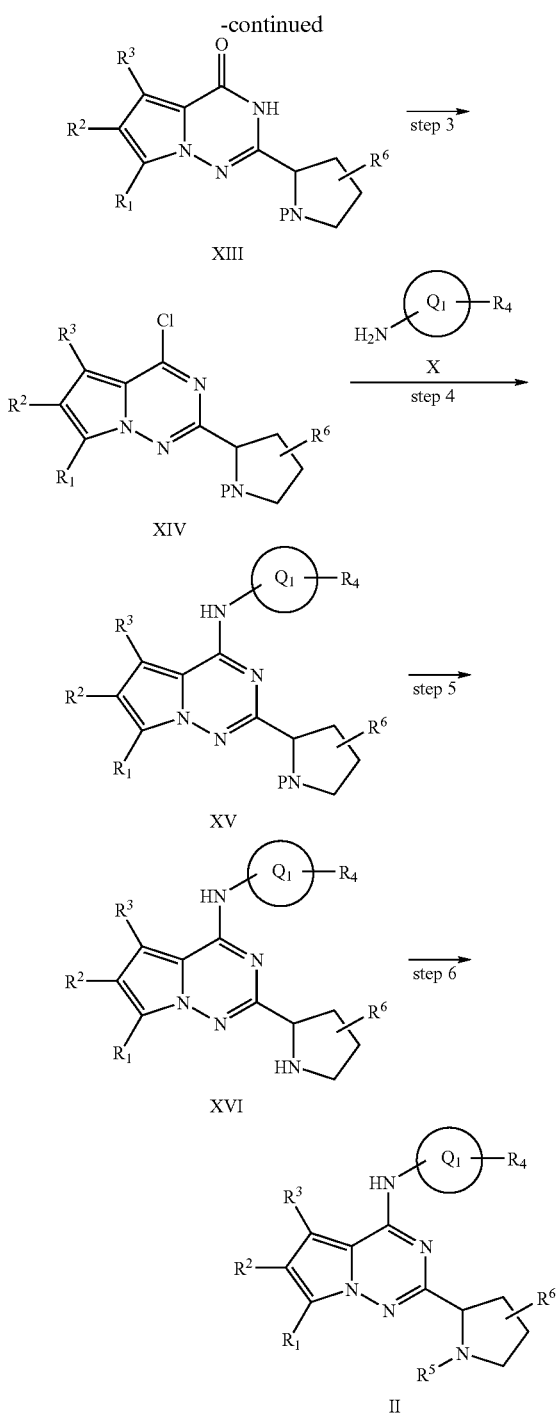

Step 1

Compound XII can be prepared by heating a mixture of the appropriately substituted 1-amino-1H-pyrrole-2-carboxamide with a protected amino acid, preferably proline or substituted proline, using any number of dehydrating agents such as DCC, EDCI, or preferably EDAC in THF resulting in the acylated derivative XII. Suitable protecting groups include those typically used to protect amino acids included benzyloxycarbonyl (Cbz) and t-butoxycarbonyl (Boc).

Step 2

The resulting acyl derivative XII can be cyclized to compound XIII using any number of dehydrating agents, most preferably aqueous KOH or phosphorous oxychloride to provide the pyrrolotriazine-4-one XIII.

Step 3

Pyrrolotriazine-4-one, XIII can then be treated with a halogenating agent, such as, for example, phosphorus oxychloride (X=Cl) or phosphorus oxybromide (X=Br), optionally in the presence of a base, such as for example, diisopropylethylamine to give compound XIV.

Step 4

Compound XIV of Scheme II is converted to compound XV by reaction with an appropriately substituted amino derivative X in the presence of a base, such as, for example, diisopropylethylamine in a solvent, such as, for example, 1-methyl-2-pyrrolidinone (NMP).

Step 5

The protecting group from Compound XV of Scheme II is removed using conditions known in the art for removal of the particular protecting group chosen to provide the unprotected amino derivative XVI.

Step 6

The amino group of Compound XVI of Scheme II can then be derivatized using conditions known in the art. It is envisioned that acyl, carbamoyl, urea, sulfonyl, alkyl, and substituted alkyl derivatives could be produced from compound XVI to provide compounds represented by compound II.

EXAMPLES

The invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the invention is not limited by the illustrative examples set forth hereinbelow, but rather defined by the claims appended hereto.

All temperatures are in degrees Celsius (° C.) unless indicated otherwise herein.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm) or using a Biotage Horizon™ HPFC™ system.

The following abbreviations are employed herein: HCl: hydrochloric acid, TFA: trifluoroacetic acid, $CH_3CN$: acetonitrile, MeOH: methanol, $MgSO_4$: magnesium sulfate, $NaHCO_3$: sodium bicarbonate, DMA: dimethylamine, $Cs_2CO_3$: cesium carbonate, $POCl_3$: phosphorous oxychloride, EtOH: ethanol, $CH_2Cl_2$: dichloromethane, NMP: 1-methyl-2-pyrrolidinone, DMF: N,N-dimethylformamide, Bn: benzyl, Me: methyl, Et: ethyl, min.: minute(s), h or hr(s): hour(s), L: liter, mL: milliliter, μL: microliter, g: gram(s), mg: milligram(s), mol.: moles, mmol: millimole(s), meq.: milliequivalent, RT or rt: room temperature, ret. t.: HPLC retention time (minutes), sat or sat'd: saturated, aq.: aqueous, TLC: thin layer chromatography, HPLC: high performance liquid chromatography, RP HPLC: reverse phase HPLC, Prep HPLC: preparative reverse phase HPLC, LC/MS: high performance liquid chromatography/mass spectrometry, MS: mass spectrometry, NMR: nuclear magnetic resonance, and mp: melting point.

Compounds with an epimerizable hydrogen at the C-2 position of the proline ring were obtained as a mixture of enantiomers that could be separated using chiral super critical fluid chromatography.

Example 1

(S)-(2-(4-(5-Cyclopropyl-1H-pyrazol-3-ylamino)pyrrolo[1,2-f][1,2,4]triazin-2-yl)pyrrolidin-1-yl)(6-fluoropyridin-3-yl)methanone

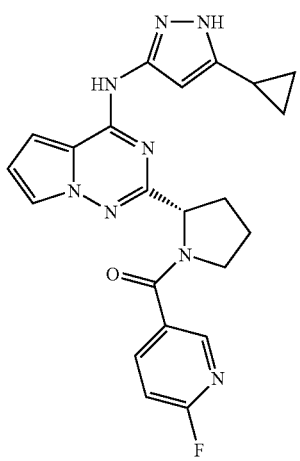

1A. (S)-tert-Butyl 2-(2-carbamoyl-1H-pyrrol-1-yl-carbamoyl)pyrrolidine-1-carboxylate

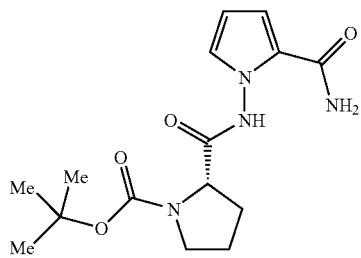

A mixture of 1-amino-1H-pyrrole-2-carboxamide (3.00 g, 24.0 mmol) and (S)-1-(tert-butoxycarbonyl)pyrrolidine-2-carboxylic acid (7.18 g, 28.8 mmol) was dissolved in THF (240 mL). To this solution was added 1-(3-dimethylaminopropyl)-3-ethylcarbodiimide hydrochloride (5.52 g, 28.8 mmol). The reaction was stirred overnight at rt, then concentrated in vacuo. The crude residue was dissolved in $CH_2Cl_2$ then washed with water (3×200 mL) and brine (200 mL). The organic layer was dried ($MgSO_4$), filtered, and concentrated in vacuo to a sticky gum, which was dissolved in a 1:1 solution of $CH_2Cl_2$/Hex, then concentrated in vacuo to remove most of the $CH_2Cl_2$. The precipitate that formed was filtered and dried to give 1A (6.68 g, 78%). 1A had an analytical HPLC retention time=2.132 min (Phenomenex Luna 3.0×50 mm, 10-90% aqueous MeOH over 5 min containing 0.1% TFA) and a LC/MS $M^++1=357$.

1B. (S)-tert-Butyl 2-(4-oxo-3,4-dihydropyrrolo[1,2-f][1,2,4]triazin-2-yl)pyrrolidine-1-carboxylate

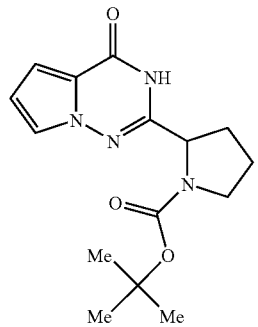

(S)-tert-Butyl 2-(2-carbamoyl-1H-pyrrol-1-ylcarbamoyl)pyrrolidine-1-carboxylate (12.46 g, 38.7 mmol) was dissolved in EtOH (194 mL). To this solution was added 1 M KOH (194 mL), and the reaction was heated to reflux for 3 d. The reaction was cooled to rt and adjusted to pH 3-4 with 1 M HCl. The resulting precipitate was filtered and dried, then dissolved in $CH_2Cl_2$ and again filtered. The filter cake was discarded, and the filtrate was concentrated in vacuo to give 1B (7.29 g, 62%). 1B had an analytical HPLC retention time=3.135 min (Phenomenex Luna 4.6×50 mm, 10-90% aqueous MeOH over 5 min containing 0.1% TFA) and a LC/MS $M^++1=305$.

1C. (S)-Benzyl 2-(4-oxo-3,4-dihydropyrrolo[1,2-f][1,2,4]triazin-2-yl)pyrrolidine-1-carboxylate

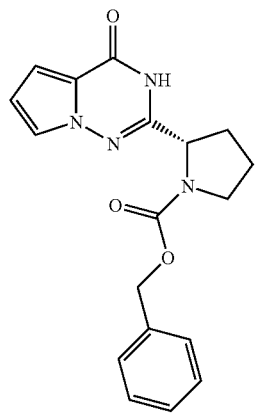

(S)-tert-Butyl-2-(4-oxo-3,4-dihydropyrrolo[1,2-f][1,2,4]triazin-2-yl)pyrrolidine-1-carboxylate (8.80 g, 28.9 mmol) was dissolved in $CH_2Cl_2$ (200 mL). To this solution was added TFA (70 mL), and the reaction was stirred at rt for 5 h. The excess TFA was removed in vacuo, then saturated $NaHCO_3$ (290 mL) was added, followed by benzyl chloroformate (8.25 mL, 57.8 mmol). The reaction was stirred overnight at rt, then EtOAc (500 mL) was added. The layers were separated, and the organic layer was washed with water (300 mL) and brine (300 mL), then dried ($MgSO_4$), filtered, and concentrated in vacuo. The crude mixture was passed through a pad of silica gel, first eluting with 4:1 Hex/EtOAc to elute excess benzyl chloroformate, then 4:1 EtOAc/Hex to elute 1C (8.49 g, 87%). 1C had an analytical HPLC retention time=2.733 min (Phenomenex Luna 3.0×50 mm, 10-90% aqueous MeOH over 5 min containing 0.1% TFA) and a LC/MS $M^++1=339$.

1D. (S)-Benzyl 2-(4-(5-cyclopropyl-1H-pyrazol-3-ylamino)pyrrolo[1,2-f][1,2,4]triazin-2-yl)pyrrolidine-1-carboxylate

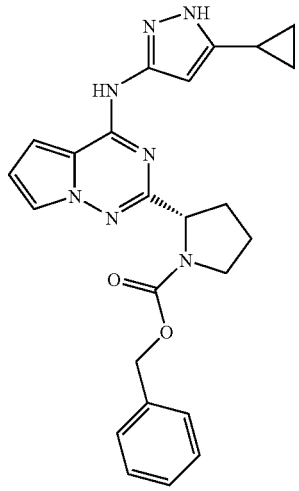

To (S)-benzyl 2-(4-oxo-3,4-dihydropyrrolo[1,2-f][1,2,4]triazin-2-yl)pyrrolidine-1-carboxylate (1.80 g, 5.32 mmol) was added POCl₃ (29.7 mL, 319 mmol). The reaction was heated to 80° C. for 1 h, then concentrated in vacuo, and repeatedly co-evaporated with toluene. The crude residue was dissolved in toluene (5 mL) and DIPEA (4.65 mL, 26.6 mmol) was added. The reaction was heated to 70° C., and a solution of 5-cyclopropyl-1H-pyrazol-3-amine (1.31 g, 10.6 mmol) in NMP (20 mL) was slowly injected. A second amount of 5-cyclopropyl-1H-pyrazol-3-amine (1.31 g, 10.6 mmol) in NMP (5 mL) was slowly injected after 50 min. The reaction was stirred at 70° C. overnight, then cooled to rt. Water (250 mL) and EtOAc (400 mL) were added, and the layers were separated. The aqueous layer was extracted with EtOAc (150 mL). The combined organic layers were washed with water (3×250 mL) and brine (250 mL), then dried (MgSO₄), filtered, and concentrated in vacuo. The compound was purified by silica gel flash chromatography (0-80% EtOAc/Hex) to give 1D (924 mg, 35%). 1D had an analytical HPLC retention time=2.716 min (Phenomenex Luna 3.0×50 mm, 10-90% aqueous MeOH over 5 min containing 0.1% TFA) and a LC/MS M⁺+1=444.

1E. (S)—N-(5-Cyclopropyl-1H-pyrazol-3-yl)-2-(pyrrolidin-2-yl)pyrrolo[1,2-f][1,2,4]triazin-4-amine

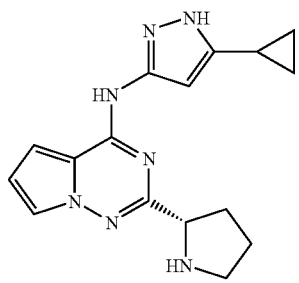

(S)-Benzyl-2-(4-(5-cyclopropyl-1H-pyrazol-3-ylamino)pyrrolo[1,2-f][1,2,4]triazin-2-yl)pyrrolidine-1-carboxylate (2.00 g, 4.51 mmol) was dissolved in MeOH (50 mL) and sparged with nitrogen. 10% Pd/C (400 mg) was added and the reaction was again sparged with nitrogen. Formic acid (88%; 9.9 mL, 226 mmol) was added, and the reaction was vigorously stirred for 2 h. The reaction was sparged with nitrogen, then filtered over diamataceous earth, washing the filter cake with MeOH. The filtrate was concentrated in vacuo and triturated with saturated aqueous NaHCO₃. The solids were filtered off, rinsed with water, and dried to give 1E (1.19 g, 85%). 1E had an analytical HPLC retention time=1.903 min (Phenomenex Luna 4.6×50 mm, 10-90% aqueous MeOH over 5 min containing 0.1% TFA) and a LC/MS M⁺+1=310.

(S)-(2-(4-(5-Cyclopropyl-1H-pyrazol-3-ylamino)pyrrolo[1,2-f][1,2,4]triazin-2-yl)pyrrolidin-1-yl)(6-fluoropyridin-3-yl)methanone (S)—N-(5-Cyclopropyl-1H-pyrazol-3-yl)-2-(pyrrolidin-2-yl)pyrrolo[1,2-f][1,2,4]triazin-4-amine (50 mg, 0.16 mmol) and 6-fluoronicotinic acid (25 mg, 0.18 mmol) were combined and dissolved in NMP (1.5 mL). To this solution was added DIPEA (85 µL, 0.49 mmol) and O-(7-azabenzotriazol-1-yl)-N,N,N',N'-tetramethyluronium hexafluorophosphate (74 mg, 0.19 mmol). The reaction was stirred at rt overnight, then separated by preparative HPLC to give the title compound (27 mg, 39%), which had an analytical HPLC retention time=1.94 min (Waters XBridge 4.6×50 mm, 5-95% aqueous acetonitrile over 5 min containing 10 mM ammonium acetate) and a LC/MS M⁺+1=433.

Example 2

(S)-(2-(4-(5-Cyclopropyl-1H-pyrazol-3-ylamino)pyrrolo[1,2-f][1,2,4]triazin-2-yl)pyrrolidin-1-yl)(thiazol-2-yl)methanone

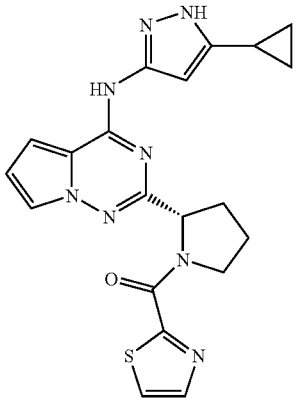

(S)—N-(5-Cyclopropyl-1H-pyrazol-3-yl)-2-(pyrrolidin-2-yl)pyrrolo[1,2-f][1,2,4]triazin-4-amine (50 mg, 0.162 mmol) was dissolved in NMP (1.5 mL). DIPEA (85 µL, 0.485 mmol) was added, followed by thiazole-2-carbonyl chloride (90% technical grade, 40 mg, ~0.24 mmol). The reaction stirred overnight at rt. The compound was purified by preparative HPLC to give the title compound (22.9 mg, 34%), which had an analytical HPLC retention time=2.02 min (Waters XBridge 4.6×50 mm, 5-95% aqueous acetonitrile over 5 min containing 10 mM ammonium acetate) and a LC/MS M⁺+1=421.

Example 3

(S)-(2-(4-(5-Cyclopropyl-1H-pyrazol-3-ylamino)pyrrolo[1,2-f][1,2,4]triazin-2-yl)pyrrolidin-1-yl)(pyrazin-2-yl)methanone

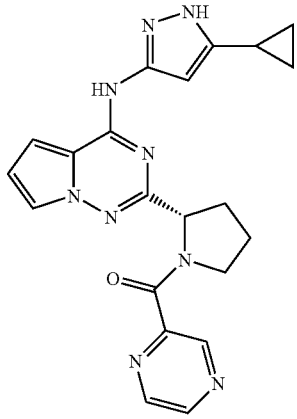

The compound was prepared analogously to Example 1 with (S)—N-(5-cyclopropyl-1H-pyrazol-3-yl)-2-(pyrrolidin-2-yl)pyrrolo[1,2-f][1,2,4]triazin-4-amine (50 mg, 0.16 mmol) and pyrazine carboxylic acid to give the title compound (10.7 mg, 16%). %), which had an analytical HPLC retention time=1.89 min (Waters XBridge 4.6×50 mm, 5-95% aqueous acetonitrile over 5 min containing 10 mM ammonium acetate) and a LC/MS $M^++1=416$.

Example 4

(S)-1-(2-(4-(5-Cyclopropyl-1H-pyrazol-3-ylamino)pyrrolo[1,2-f][1,2,4]-triazin-2-yl)pyrrolidin-1-yl)ethanone

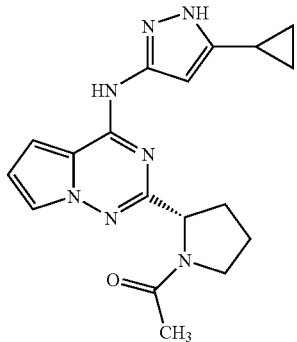

(S)—N-(5-Cyclopropyl-1H-pyrazol-3-yl)-2-(pyrrolidin-2-yl)pyrrolo[1,2-f][1,2,4]triazin-4-amine (50 mg, 0.162 mmol) was dissolved in pyridine (1 mL). Acetic anhydride (16.8 μL, 0.178 mmol) was added, and the reaction was stirred at rt for 2 h. The compound was purified by preparative HPLC to give the title compound (22 mg, 38%), which had an analytical HPLC retention time=2.138 min (Phenomenex Luna 3.0×50 mm, 10-90% aqueous MeOH over 5 min containing 0.1% TFA) and a LC/MS $M^++1=352$.

Examples 5 and 6

(S)-tert-Butyl 4-(2-(4-(5-cyclopropyl-1H-pyrazol-3-ylamino)pyrrolo[1,2-f][1,2,4]triazin-2-yl)pyrrolidine-1-carbonyl)piperidine-1-carboxylate and (S)-(2-(4-(5-Cyclopropyl-1H-pyrazol-3-ylamino)pyrrolo[1,2-f][1,2,4]triazin-2-yl)pyrrolidin-1-yl)(piperidin-4-yl)methanone Example 5

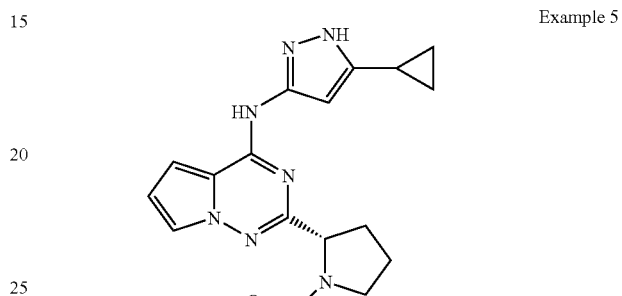

Example 6

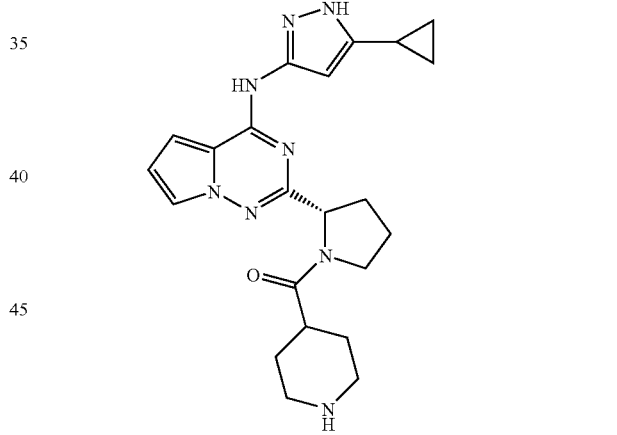

(S)—N-(5-Cyclopropyl-1H-pyrazol-3-yl)-2-(pyrrolidin-2-yl)pyrrolo[1,2-f][1,2,4]triazin-4-amine (100 mg, 0.323 mmol) and 1-(tert-butoxycarbonyl)piperidine-4-carboxylic acid (81 mg, 0.355 mmol) were combined and dissolved in NMP (3 mL). To this solution was added DIPEA (169 μL, 0.969 mmol) and O-(7-azabenzotriazol-1-yl)-N,N,N',N'-tetramethyluronium hexafluorophosphate (148 mg, 0.388 mmol). The reaction was stirred at room temperature for 3 d, then EtOAc (50 mL) was added. The reaction was washed with water (2×50 mL) and brine (50 mL), then dried (MgSO$_4$), filtered, and concentrated in vacuo. The compound was purified by preparative HPLC. Partial removal of the tert-butyl carbamate resulted. A second purification by preparative HPLC was performed to give the title compounds (Example 5, 29.2 mg; Example 6, 17.0 mg). Example 5 had an analytical HPLC retention time=2.19 min (Waters XBridge 4.6×50 mm, 5-95% aqueous acetonitrile over 5 min containing 10 mM ammonium acetate) and a LC/MS M$^+$+1=521. Example 6 had an analytical HPLC retention time=1.58 min (Waters XBridge 4.6×50 mm, 5-95% aqueous acetonitrile over 5 min containing 10 mM ammonium acetate) and a LC/MS M$^+$+1=421.

Example 7

(S)-(2-(4-(5-Cyclopropyl-1H-pyrazol-3-ylamino)pyrrolo[1,2-f][1,2,4]triazin-2-yl)pyrrolidin-1-yl)(1H-pyrazol-3-yl)methanone

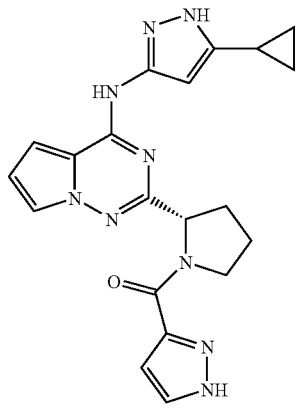

The compound was prepared analogously to Example 1 with (S)—N-(5-cyclopropyl-1H-pyrazol-3-yl)-2-(pyrrolidin-2-yl)pyrrolo[1,2-f][1,2,4]triazin-4-amine (50 mg, 0.16 mmol) and 1H-pyrazole-3-carboxylic acid to give the title compound (21.5 mg, 33%), which had an analytical HPLC retention time=1.76 min (Waters XBridge 4.6×50 mm, 5-95% aqueous acetonitrile over 3 min containing 10 mM ammonium acetate) and a LC/MS M$^+$+1=404.

Example 8

(S)-(2-(4-(5-Cyclopropyl-1H-pyrazol-3-ylamino)pyrrolo[1,2-f][1,2,4]triazin-2-yl)pyrrolidin-1-yl)(pyridin-3-yl)methanone

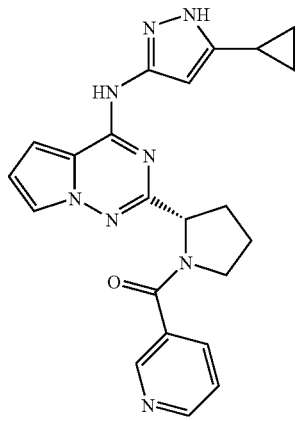

The compound was prepared analogously to Example 2 with (S)—N-(5-cyclopropyl-1H-pyrazol-3-yl)-2-(pyrrolidin-2-yl)pyrrolo[1,2-f][1,2,4]triazin-4-amine (100 mg, 0.32 mmol) and nicotinoyl chloride hydrochloride (58 mg, 0.32 mmol) to give the title compound (80 mg, 60%), which had an analytical HPLC retention time=1.76 min (Phenomenex Luna 3.0×50 mm, 10-90% aqueous MeOH over 6 min containing 0.1% TFA) and a LC/MS M$^+$+1=415.

Example 9

(S)—N-(5-Cyclopropyl-1H-pyrazol-3-yl)-2-(1-(pyridin-3-ylsulfonyl)pyrrolidin-2-yl)pyrrolo[1,2-f][1,2,4]triazin-4-amine

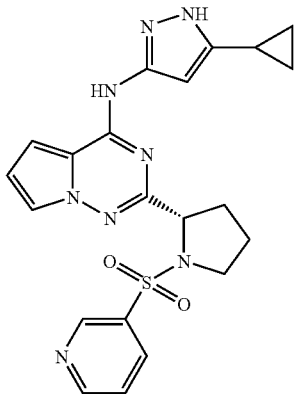

(S)—N-(5-Cyclopropyl-1H-pyrazol-3-yl)-2-(pyrrolidin-2-yl)pyrrolo[1,2-f][1,2,4]triazin-4-amine (150 mg, 0.485 mmol) was dissolved in NMP (4 mL), to which was added DIPEA (254 µL, 1.45 mmol) and pyridine-3-sulfonyl chloride hydrochloride (Karaman, R. et al. *J. Am. Chem. Soc.* 1992, 114, 4889-4898; 104 mg, 0.485 mmol). The reaction was stirred at rt for 30 min, then EtOAc was added (100 mL). The reaction mixture was washed with water (3×100 mL) and brine (100 mL). The organic layer was dried (MgSO$_4$), filtered, and concentrated in vacuo. The compound was purified by preparative HPLC to give the title compound (104 mg, 47%), which had an analytical HPLC retention time=1.97 min (Waters XBridge 4.6×50 mm, 5-95% aqueous acetonitrile over 5 min containing 10 mM ammonium acetate) and a LC/MS M$^+$+1=451.

Example 10

(S)-5-(4-(5-Cyclopropyl-1H-pyrazol-3-ylamino)pyrrolo[1,2-f][1,2,4]triazin-2-yl)-1-(6-fluoronicotinoyl)pyrrolidin-2-one

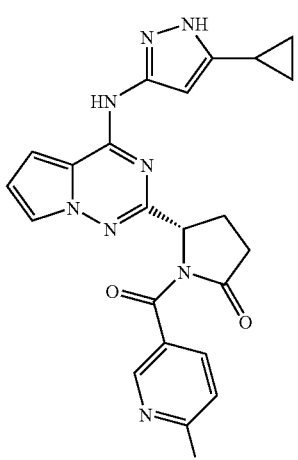

10A. (S)-tert-Butyl 4-(tert-butoxycarbonylamino)-5-(2-carbamoyl-1H-pyrrol-1-ylamino)-5-oxopentanoate

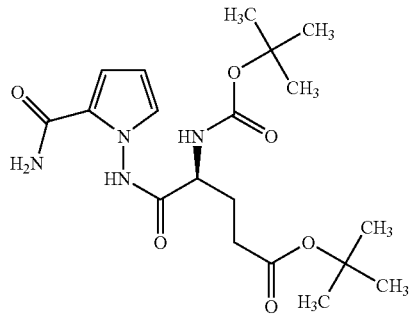

A mixture of 1-amino-1H-pyrrole-2-carboxamide (1.00 g, 7.99 mmol) and (S)-5-tert-butoxy-2-(tert-butoxycarbonylamino)-5-oxopentanoic acid (2.91 g, 9.59 mmol) was dissolved in THF (80 mL). To this solution was added 1-(3-dimethylaminopropyl)-3-ethylcarbodiimide hydrochloride (1.84 g, 9.59 mmol). The reaction was stirred at rt for 1.5 h, then concentrated in vacuo. $CH_2Cl_2$ (150 mL) was added, and the reaction mixture was washed with water (2×150 mL). The organic layer was dried ($MgSO_4$), filtered, and concentrated in vacuo. The compound was purified by silica gel flash chromatography (0-35% 90:10:1 [$CH_2Cl_2$/MeOH/conc $NH_4OH$]/$CH_2Cl_2$) to give 10A (2.90 g, 85%). 10A had an analytical HPLC retention time=2.05 min (Waters XBridge 4.6×50 mm, 5-95% aqueous acetonitrile over 5 min containing 10 mM ammonium acetate) and a LC/MS $M^--1=409$.

10B. (S)-4-(tert-Butoxycarbonylamino)-4-(4-oxo-3,4-dihydropyrrolo[1,2-f][1,2,4]triazin-2-yl)butanoic acid

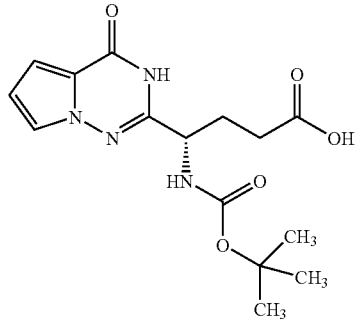

(S)-tert-Butyl 4-(tert-butoxycarbonylamino)-5-(2-carbamoyl-1H-pyrrol-1-ylamino)-5-oxopentanoate (3.79 g, 9.23 mmol) was dissolved in EtOH (90 mL), to which was added 1 M KOH (90 mL). The reaction mixture was heated to reflux overnight, cooled to rt, adjusted to pH 3 with 1 M HCl, and extracted with EtOAc (2×150 mL). The combined organic layers were washed with brine (200 mL), dried ($MgSO_4$), filtered, and concentrated in vacuo to give slightly impure 10B (3.16 g, >100%). 10B had an analytical HPLC retention time=2.472 min (Phenomenex Luna 4.6×50 mm, 10-90% aqueous MeOH over 5 min containing 0.1% TFA) and a LC/MS $M^++1=337$.

10C. (S)-Methyl 4-amino-4-(4-oxo-3,4-dihydropyrrolo[1,2-f][1,2,4]triazin-2-yl)butanoate dihydrochloride

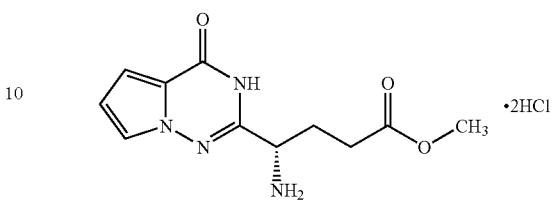

(S)-4-(tert-Butoxycarbonylamino)-4-(4-oxo-3,4-dihydropyrrolo[1,2-f][1,2,4]triazin-2-yl)butanoic acid (3.47 g, ~10.3 mmol) was dissolved in MeOH (150 mL). Acetyl chloride (7.32 mL, 103 mmol) was added, and the reaction was stirred overnight at rt. The reaction was concentrated in vacuo. The crude residue was dissolved in MeOH and treated with activated carbon, then filtered. The filtrate was concentrated in vacuo to give slightly impure 10C (2.67 g, ~80%). 10C had an analytical HPLC retention time=2.16 min (Waters XBridge 4.6×50 mm, 5-95% aqueous acetonitrile over 5 min containing 10 mM ammonium acetate) and a LC/MS $M^++1=251$.

10D. (S)-Methyl 4-amino-4-(4-(5-cyclopropyl-1H-pyrazol-3-ylamino)pyrrolo[1,2-f][1,2,4]triazin-2-yl)butanoate

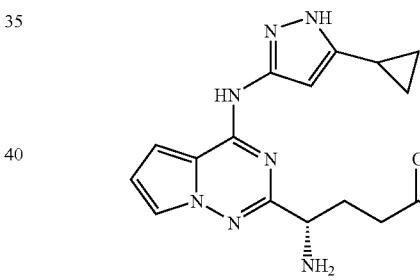

(S)-Methyl-4-amino-4-(4-oxo-3,4-dihydropyrrolo[1,2-f][1,2,4]triazin-2-yl)butanoate dihydrochloride (2.65 g, ~8.2 mmol) was dissolved in $POCl_3$ (40 mL, 430 mmol) and heated to 80° C. for 7 h. The reaction was concentrated in vacuo, co-evaporating several times with toluene. The residue was dissolved in NMP (30 mL) and heated to 80° C. A solution of 5-cyclopropyl-1H-pyrazol-3-amine (5.05 g, 41 mmol) dissolved in NMP (10 mL) was slowly injected. The reaction was stirred overnight at 80° C., then cooled to rt. EtOAc (800 mL) was added, and the reaction was extracted with water (2×500 mL). The organic layer was discarded. The combined aqueous layers were adjusted to pH 7 with 1 M NaOH and extracted with EtOAc (3×300 mL). The combined extracts were dried ($MgSO_4$), filtered, and concentrated in vacuo. The compound was purified by silica gel flash chromatography (0-100% 90:10:1 [$CH_2Cl_2$/MeOH/conc $NH_4OH$]/$CH_2Cl_2$) to give slightly impure 10D (1.70 g, ~50%). 10D had an analytical HPLC retention time=2.322 min (Phenomenex Luna 4.6×50 mm, 10-90% aqueous MeOH over 5 min containing 0.1% TFA) and a LC/MS $M^++1=356$.

10E. (S)-Methyl 4-(4-(5-cyclopropyl-1H-pyrazol-3-ylamino)pyrrolo[1,2-f][1,2,4]triazin-2-yl)-4-(6-fluoronicotinamido)butanoate

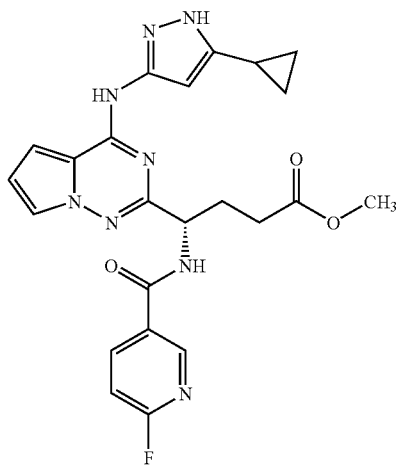

Slightly impure (S)-Methyl 4-amino-4-(4-(5-cyclopropyl-1H-pyrazol-3-ylamino)pyrrolo[1,2-f][1,2,4]triazin-2-yl)butanoate (330 mg, ~0.9 mmol) was dissolved in NMP (5 mL), to which was added DIPEA (524 μL, 3.00 mmol), 6-fluoronicotinic acid (141 mg, 1.10 mmol), and O-(7-azabenzotriazol-1-yl)-N,N,N', N'-tetramethyluronium hexafluorophosphate (456 mg, 1.20 mmol). The reaction was stirred at rt for 20 min, then EtOAc (100 mL) was added. The organics were washed with water (2×100 mL) and brine (100 mL), then dried (MgSO$_4$), filtered, and concentrated in vacuo. The compound was purified by silica gel flash chromatography (0-50% 90:10:1 [CH$_2$Cl$_2$/MeOH/conc NH$_4$OH]/CH$_2$Cl$_2$) to give 10E (188 mg, 40%). 10E had an analytical HPLC retention time=1.97 min (Waters XBridge 4.6×50 mm, 5-95% aqueous acetonitrile over 5 min containing 10 mM ammonium acetate) and a LC/MS M$^+$+1=479.

10F. (S)-4-(4-(5-Cyclopropyl-1H-pyrazol-3-ylamino)pyrrolo[1,2-f][1,2,4]triazin-2-yl)-4-(6-fluoronicotinamido)butanoic acid

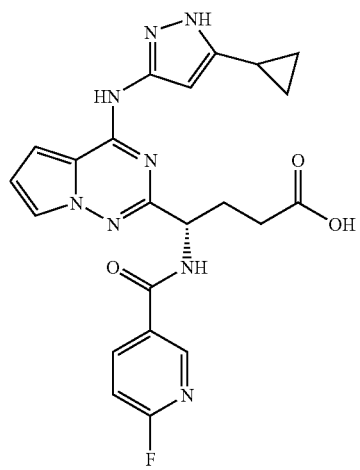

(S)-Methyl 4-(4-(5-cyclopropyl-1H-pyrazol-3-ylamino)pyrrolo[1,2-f][1,2,4]triazin-2-yl)-4-(6-fluoronicotinamido)butanoate (94.0 mg, 0.196 mmol) was dissolved in THF (1 mL). A solution of lithium hydroxide hydrate (25.0 mg, 0.589 mmol) in water (1 mL) was added, and the reaction was stirred at rt for 30 min. The reaction was adjusted to pH 6 with 1 M HCl and extracted with EtOAc (2×10 mL). The aqueous layer was adjusted to pH 3 with 1 M HCl, then extracted again with EtOAc (10 mL). The combined organic layers were dried (MgSO$_4$), filtered, and concentrated in vacuo to give 10F (81.0 mg, 89%). 10F had an analytical HPLC retention time=2.638 min (Phenomenex Luna 4.6×50 mm, 10-90% aqueous MeOH over 5 min containing 0.1% TFA) and a LC/MS M$^+$+1=465.

(S)-4-(tert-Butoxycarbonylamino)-4-(4-oxo-3,4-dihydropyrrolo[1,2-f][1,2,4]triazin-2-yl)butanoic acid (S)-4-(4-(5-Cyclopropyl-1H-pyrazol-3-ylamino)pyrrolo[1,2-f][1,2,4]triazin-2-yl)-4-(6-fluoronicotinamido)butanoic acid (81.0 mg, 0.174 mmol) was suspended in THF (1 mL), then pyridine (17 μL, 0.21 mmol) and pentafluorophenol trifluoroacetate (33 μL, 0.19 mmol) was added. After stirring several min at rt, more pyridine (51 μL, 0.63 mmol) and pentafluorophenol trifluoroacetate (100 μL, 0.57 mmol) were added. After stirring several more min at rt, the reaction was diluted with CH$_2$Cl$_2$ (10 mL), then washed with 0.1 M HCl (10 mL) and 5% aqueous NaHCO$_3$ (10 mL). The organic layer was dried (MgSO$_4$), filtered, and concentrated in vacuo to give an oily residue. This residue was dissolved in THF (4 mL), acetonitrile (1.5 mL), and 0.1 M NaHCO$_3$ (4 mL). After 2 h, Na$_2$CO$_3$ (100 mg) was added. The reaction was stirred for 1 h at rt, then diluted with EtOAc (80 mL). The reaction was washed with water (50 mL), and the aqueous layer was extracted with EtOAc (50 mL). The combined organic layers were washed with brine (100 mL), dried (MgSO$_4$), filtered, and concentrated in vacuo. The compound was purified by preparative HPLC to give the title compound (13.5 mg, 17%), which had an analytical HPLC retention time=2.250 min (Phenomenex Luna 3.0×50 mm, 10-90% aqueous MeOH over 5 min containing 0.1% TFA) and a LC/MS M$^+$+1=447.

Example 11

(R)-(2-(4-(5-Cyclopropyl-1H-pyrazol-3-ylamino)pyrrolo[1,2-f][1,2,4]triazin-2-yl)pyrrolidin-1-yl)(6-fluoropyridin-3-yl)methanone

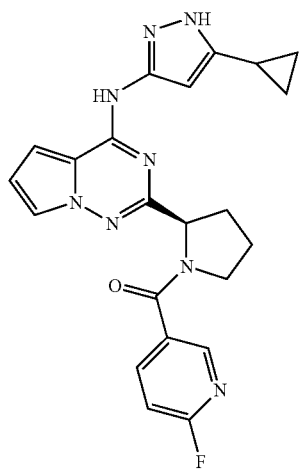

11A. (R)-Benzyl 2-(2-carbamoyl-1H-pyrrol-1-ylcarbamoyl)pyrrolidine-1-carboxylate

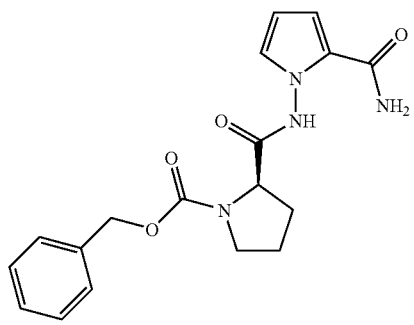

A mixture of 1-amino-1H-pyrrole-2-carboxamide (6.00 g, 48.0 mmol) and (R)-1-(benzyloxycarbonyl)pyrrolidine-2-carboxylic acid (14.3 g, 57.5 mmol) was dissolved in THF (480 mL). To this solution was added 1-(3-dimethylaminopropyl)-3-ethylcarbodiimide hydrochloride (11.0 g, 57.5 mmol). The reaction was stirred overnight at rt then concentrated in vacuo. The residue was dissolved in $CH_2Cl_2$ (400 mL), washed with water (3×400 mL) and brine (400 mL), then dried ($MgSO_4$), filtered, and concentrated in vacuo to give slightly impure 11A (17.65 g, >100%). 11A had an analytical HPLC retention time=2.103 min (Phenomenex Luna 3.0×50 mm, 10-90% aqueous MeOH over 5 min containing 0.1% TFA) and a LC/MS $M^++1=357$.

11B. (R)-Benzyl 2-(4-oxo-3,4-dihydropyrrolo[1,2-f][1,2,4]triazin-2-yl)pyrrolidine-1-carboxylate

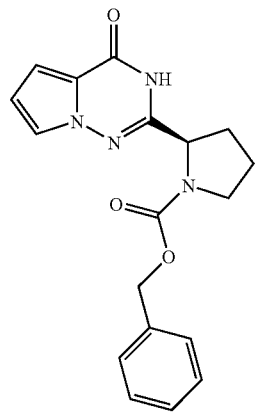

(R)-Benzyl 2-(2-carbamoyl-1H-pyrrol-1-ylcarbamoyl)pyrrolidine-1-carboxylate (17.6 g, 48.0 mmol) was dissolved in EtOH (240 mL). 1 M KOH (240 mL, 240 mmol) was added, and the reaction was heated to reflux for 3 d. The reaction was concentrated in vacuo to remove most of the EtOH, then adjusted to pH 9 with conc HCl. The reaction mixture was extracted with EtOAc (2×150 mL), and the combined extracts were dried ($MgSO_4$), filtered, and concentrated in vacuo to give 11B (6.76 g, 42%). 11B had an analytical HPLC retention time=2.733 min (Phenomenex Luna 3.0×50 mm, 10-90% aqueous MeOH over 5 min containing 0.1% TFA) and a LC/MS $M^++1=339$.

11C. (R)-Benzyl 2-(4-(5-cyclopropyl-1H-pyrazol-3-ylamino)pyrrolo[1,2-f][1,2,4]triazin-2-yl)pyrrolidine-1-carboxylate

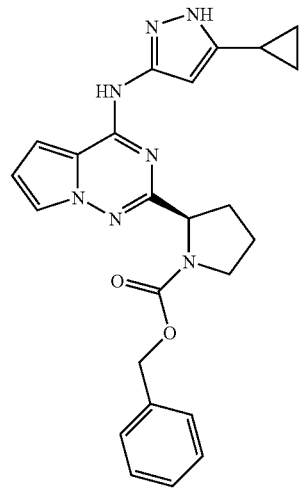

To (R)-benzyl 2-(4-oxo-3,4-dihydropyrrolo[1,2-f][1,2,4]triazin-2-yl)pyrrolidine-1-carboxylate (6.60 g, 19.5 mmol) was added $POCl_3$ (109 mL, 1170 mmol). The reaction was heated to 80° C. for 1 h, then concentrated in vacuo and co-evaporated with toluene several times. The crude residue was dissolved in toluene (70 mL), and DIPEA (17.0 mL, 97.5 mmol) was added. The reaction was heated to 70° C. then a solution of 5-cyclopropyl-1H-pyrazol-3-amine (9.60 g, 78.0 mmol) in NMP (130 mL) was slowly injected over 30 min. The reaction was stirred at 70° C. overnight, then cooled to rt. EtOAc (1000 mL) was added, and the reaction was washed with water (4×500 mL), dried ($MgSO_4$), filtered, and concentrated in vacuo. The compound was purified by silica gel flash chromatography (5-70% EtOAc/Hex) to give 11C (3.88 g, 44%). 11C had an analytical HPLC retention time=3.726 min (Phenomenex Luna 3.0×50 mm, 10-90% aqueous MeOH over 5 min containing 0.1% TFA) and a LC/MS $M^++1=444$.

11D. (R)—N-(5-Cyclopropyl-1H-pyrazol-3-yl)-2-(pyrrolidin-2-yl)pyrrolo[1,2-f][1,2,4]triazin-4-amine

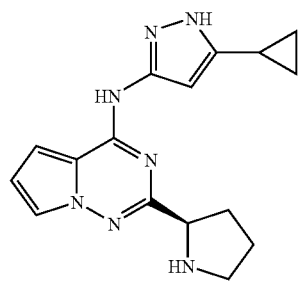

(R)-Benzyl-2-(4-(5-cyclopropyl-1H-pyrazol-3-ylamino)pyrrolo[1,2-f][1,2,4]triazin-2-yl)pyrrolidine-1-carboxylate (3.80 g, 4.51 mmol) was dissolved in MeOH (85 mL) and sparged with nitrogen. 10% Palladium on carbon (1.0 g) was added and the reaction was again sparged with nitrogen. Formic acid (88%, 19.0 mL, 430 mmol) was added, and the reaction was vigorously stirred for 50 min. The reaction was sparged with nitrogen, then filtered over diatomaceous earth, washing the filter cake with MeOH. The filtrate was concentrated in vacuo and triturated with saturated aqueous NaHCO$_3$. The solids were filtered off, rinsed with water, and dried to give 11D (2.16 g, 81%). 11D had an analytical HPLC retention time=1.927 min (Phenomenex Luna 3.0×50 mm, 10-90% aqueous MeOH over 5 min containing 0.1% TFA) and a LC/MS M$^+$+1=310.

(R)-(2-(4-(5-Cyclopropyl-1H-pyrazol-3-ylamino) pyrrolo[1,2-f][1,2,4]triazin-2-yl)pyrrolidin-1-yl)(6-fluoropyridin-3-yl)methanone (R)—N-(5-Cyclopropyl-1H-pyrazol-3-yl)-2-(pyrrolidin-2-yl)pyrrolo[1,2-f][1,2,4]triazin-4-amine (50 mg, 0.16 mmol) and 6-fluoronicotinic acid (25 mg, 0.18 mmol) were combined and dissolved in NMP (1.5 mL). To this solution was added DIPEA (85 µL, 0.49 mmol) and O-(7-azabenzotriazol-1-yl)-N,N,N',N'-tetramethyluronium hexafluorophosphate (74 mg, 0.19 mmol). The reaction was stirred at rt overnight, then EtOAc (50 mL) was added. The reaction was washed with water (3×50 mL) and brine (50 mL) then dried (MgSO$_4$), filtered, and concentrated in vacuo. The compound was purified by preparative HPLC to give the title compound (40 mg, 57%), which had an analytical HPLC retention time=1.92 min (Waters XBridge 4.6×50 mm, 5-95% aqueous acetonitrile over 5 min containing 10 mM ammonium acetate) and a LC/MS M$^+$+1=433.

Example 12

(R)-(2-(4-(5-Cyclopropyl-1H-pyrazol-3-ylamino) pyrrolo[1,2-f][1,2,4]triazin-2-yl)pyrrolidin-1-yl) (pyrazin-2-yl)methanone

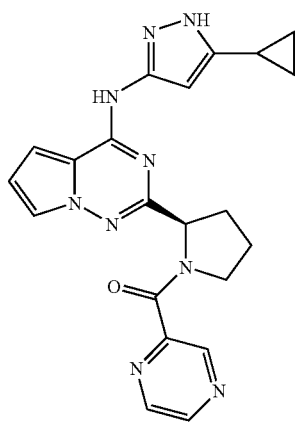

The compound was produced analogously to Example 11 with (R)—N-(5-cyclopropyl-1H-pyrazol-3-yl)-2-(pyrrolidin-2-yl)pyrrolo[1,2-f][1,2,4]triazin-4-amine (50 mg, 0.16 mmol) and pyrazine carboxylic acid (22 mg, 0.18 mmol) to give the title compound (32 mg, 47%), which had an analytical HPLC retention time=1.81 min (Waters XBridge 4.6×50 mm, 5-95% aqueous acetonitrile over 5 min containing 10 mM ammonium acetate) and a LC/MS M$^+$+1=416.

Example 13

(R)-tert-Butyl 4-(2-(4-(5-cyclopropyl-1H-pyrazol-3-ylamino)pyrrolo[1,2-f][1,2,4]triazin-2-yl)pyrrolidine-1-carbonyl)piperidine-1-carboxylate

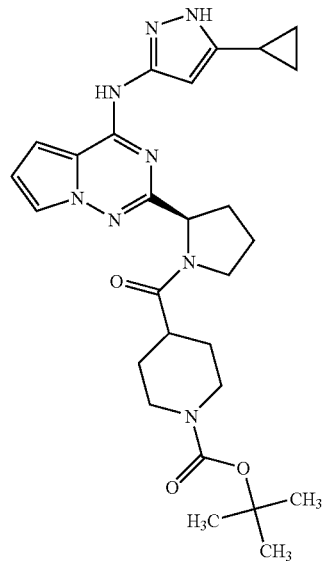

The compound was produced analogously to Example 11 with (R)—N-(5-cyclopropyl-1H-pyrazol-3-yl)-2-(pyrrolidin-2-yl)pyrrolo[1,2-f][1,2,4]triazin-4-amine (100 mg, 0.323 mmol) and 1-(tert-butoxycarbonyl)piperidine-4-carboxylic acid (81 mg, 0.36 mmol), except that only one quarter of the crude material was purified to give the title compound (25 mg, 15%), which had an analytical HPLC retention time=2.18 min (Waters XBridge 4.6×50 mm, 5-95% aqueous acetonitrile over 5 min containing 10 mM ammonium acetate) and a LC/MS M$^+$+1=521.

Example 14

(R)-(2-(4-(5-Cyclopropyl-1H-pyrazol-3-ylamino) pyrrolo[1,2-f][1,2,4]triazin-2-yl)pyrrolidin-1-yl)(piperidin-4-yl)methanone

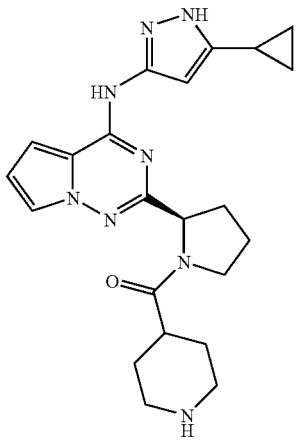

Slightly impure (R)-tert-butyl 4-(2-(4-(5-cyclopropyl-1H-pyrazol-3-ylamino)pyrrolo[1,2-f][1,2,4]triazin-2-yl)pyrrolidine-1-carbonyl)piperidine-1-carboxylate (91 mg, 0.13 mmol) was dissolved in CH$_2$Cl$_2$ (2 mL), to which was added TFA (2 mL). The reaction was stirred at rt for 2 h, then concentrated in vacuo. The compound was purified by preparative HPLC to give the title compound (22 mg, 40%), which had an analytical HPLC retention time=1.69 min (Waters XBridge 4.6×50 mm, 5-95% aqueous acetonitrile over 5 min containing 10 mM ammonium acetate) and a LC/MS $M^++1=421$.

Example 15

(R)-(2-(4-(5-Cyclopropyl-1H-pyrazol-3-ylamino) pyrrolo[1,2-f][1,2,4]triazin-2-yl)pyrrolidin-1-yl) (thiazol-2-yl)methanone

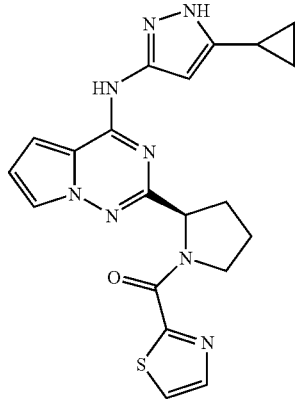

(R)—N-(5-Cyclopropyl-1H-pyrazol-3-yl)-2-(pyrrolidin-2-yl)pyrrolo[1,2-f][1,2,4]triazin-4-amine (50 mg, 0.16 mmol) was dissolved in NMP (1.5 mL). DIPEA (85 μL, 0.49 mmol) was added, followed by thiazole-2-carbonyl chloride (90% technical grade, 40 mg, ~0.24 mmol). The reaction was stirred for 3 h at rt, then EtOAc (50 mL) was added. The reaction was washed with water (3×50 mL) and brine (50 mL), then dried (MgSO₄), filtered, and concentrated in vacuo. The compound was purified by preparative HPLC to give the title compound (48 mg, 70%), which had an analytical HPLC retention time=2.04 min (Waters XBridge 4.6×50 mm, 5-95% aqueous acetonitrile over 5 min containing 10 mM ammonium acetate) and a LC/MS $M^++1=421$.

Example 16

(R)-2-(4-(5-Cyclopropyl-1H-pyrazol-3-ylamino) pyrrolo[1,2-f][1,2,4]triazin-2-yl)-N-(6-fluoropyridin-3-yl)pyrrolidine-1-carboxamide

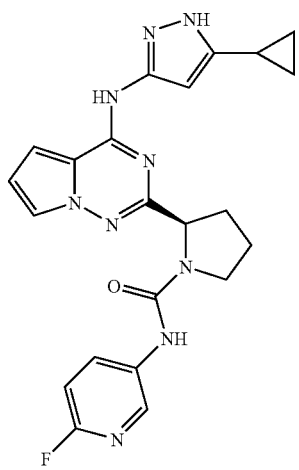

16A. Phenyl 6-fluoropyridin-3-ylcarbamate

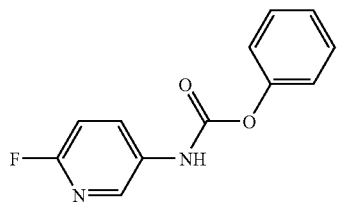

6-Fluoropyridin-3-amine (224 mg, 2.00 mmol) was dissolved in THF (4 mL). Pyridine (202 μL, 2.50 mmol) was added, followed by phenyl chloroformate (258 μL, 2.06 mmol). The reaction was stirred at rt for 2 h, then EtOAc (20 mL) was added. The reaction was washed with 1 M HCl (10 mL), water (10 mL), saturated aqueous NaHCO₃ (10 mL), and brine (10 mL), then dried (MgSO₄), filtered, and concentrated in vacuo to give slightly impure 16A (471 mg, >100%). 16A had an analytical HPLC retention time=2.437 min (Phenomenex Luna 3.0×50 mm, 10-90% aqueous MeOH over 5 min containing 0.1% TFA) and a LC/MS $M^++1=233$.

(R)-2-(4-(5-Cyclopropyl-1H-pyrazol-3-ylamino) pyrrolo[1,2-f][1,2,4]triazin-2-yl)-N-(6-fluoropyridin-3-yl)pyrrolidine-1-carboxamide (R)—N-(5-Cyclopropyl-1H-pyrazol-3-yl)-2-(pyrrolidin-2-yl)pyrrolo[1,2-f][1,2,4]triazin-4-amine (250 mg, 0.808 mmol) was dissolved in DMSO (1.6 mL), to which was added slightly impure phenyl 6-fluoropyridin-3-ylcarbamate (175 mg, ~0.770 mmol). The reaction was stirred at rt for 1.5 h, then EtOAc (100 mL) was added. The reaction was washed with water (2×100 mL), then dried (MgSO₄), filtered, and concentrated in vacuo. The compound was purified by silica gel flash chromatography (10-80% 90:10:1 [CH₂Cl₂/MeOH/ conc NH₄OH]/CH₂Cl₂) to give the title compound (246 mg, 68%), which had an analytical HPLC retention time=1.93 min (Waters XBridge 4.6×50 mm, 5-95% aqueous acetonitrile over 5 min containing 10 mM ammonium acetate) and a LC/MS $M^++1=448$.

Examples 17 and 18

(1R,2R)-2-(4-(5-Cyclopropyl-1H-pyrazol-3-ylamino)pyrrolo[1,2-f][1,2,4]triazin-2-yl)-N-(6-fluoropyridin-3-yl)cyclopentanecarboxamide and (1S,2S)-2-(4-(5-Cyclopropyl-1H-pyrazol-3-ylamino) pyrrolo[1,2-f][1,2,4]triazin-2-yl)-N-(6-fluoropyridin-3-yl)cyclopentanecarboxamide Example 17

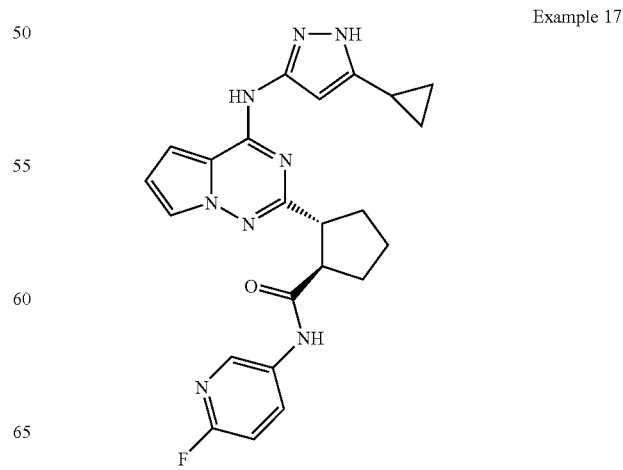

Example 18

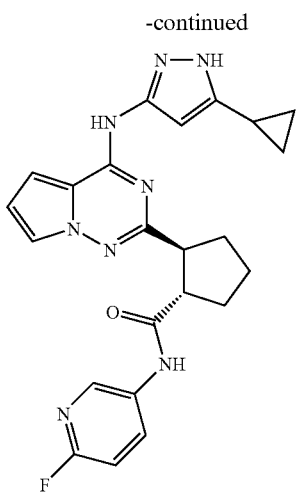

17/18A. trans-Methyl 2-(2-carbamoyl-1H-pyrrol-1-ylcarbamoyl)cyclopentanecarboxylate

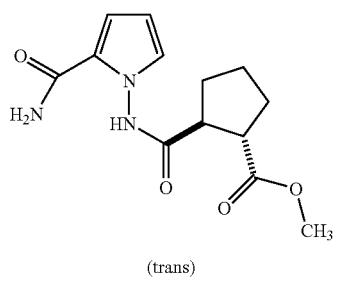
(trans)

A mixture of 1-amino-1H-pyrrole-2-carboxamide (363 mg, 2.90 mmol) and trans-2-(methoxycarbonyl)cyclopentanecarboxylic acid (Samuelsson, B. et al. *J. Med. Chem.* 2000, 43, 1705-1713; 550 mg, 3.19 mmol) was dissolved in THF (25 mL). To this solution was added 1-(3-dimethylaminopropyl)-3-ethylcarbodiimide hydrochloride (612 mg, 3.19 mmol). The reaction was stirred overnight at rt, then EtOAc (100 mL) was added. The reaction was washed with water (100 mL), and the aqueous layer was extracted with EtOAc (2×100 mL). The combined organic layers were dried (MgSO$_4$), filtered, and concentrated in vacuo. The compound was purified by silica gel flash chromatography (0-50% 90:10:1 [CH$_2$Cl$_2$/MeOH/conc NH$_4$OH]/CH$_2$Cl$_2$) to give 17A/18A (587 mg, 72%). 17A/18A had an analytical HPLC retention time=1.71 min (Waters XBridge 4.6×50 mm, 5-95% aqueous acetonitrile over 5 min containing 10 mM ammonium acetate) and a LC/MS M$^-$−1=278.

17/18B. trans-2-(4-Oxo-3,4-dihydropyrrolo[1,2-f][1,2,4]triazin-2-yl)cyclopentanecarboxylic acid

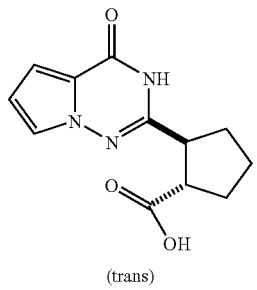
(trans)

trans-Methyl 2-(2-carbamoyl-1H-pyrrol-1-ylcarbamoyl)cyclopentane carboxylate (575 mg, 2.06 mmol) was dissolved in EtOH (20 mL), to which was added 1 M KOH (20.0 mL, 20.0 mmol). The reaction was heated to reflux for 6 h, then cooled to rt. water (50 mL) was added, and the reaction was adjusted to pH 3 with 1 M HCl. The mixture was extracted with EtOAc (2×100 mL), and the combined organics were dried (MgSO$_4$), filtered, and concentrated in vacuo to give slightly impure 17/18B (463 mg, 90%). 17/18B had an analytical HPLC retention time=2.430 min (Phenomenex Luna 4.6×50 mm, 10-90% aqueous MeOH over 5 min containing 0.1% TFA) and a LC/MS M$^+$+1=248.

17/18C. trans-Methyl 2-(4-oxo-3,4-dihydropyrrolo[1,2-f][1,2,4]triazin-2-yl)cyclopentanecarboxylate hydrochloride

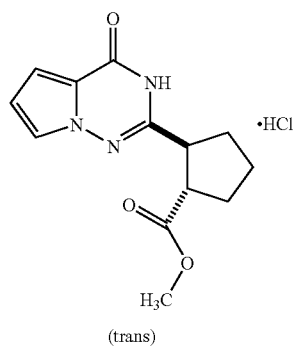
(trans)

trans-2-(4-Oxo-3,4-dihydropyrrolo[1,2-f][1,2,4]triazin-2-yl)cyclopentanecarboxylic acid (455 mg, 1.84 mmol) was dissolved in MeOH (18 mL). Acetyl chloride (131 µL, 1.84 mmol) was added, and the reaction was stirred overnight at rt. More acetyl chloride (262 µL, 3.68 mmol) was added, and the reaction was stirred for several more min before concentrating in vacuo to give 17/18C (462 mg, 84%). 17/18C had an analytical HPLC retention time=2.233 min (Phenomenex Luna 3.0×50 mm, 10-90% aqueous MeOH over 5 min containing 0.1% TFA) and a LC/MS M$^+$+1=262.

17/18D. trans-Methyl 2-(4-(5-cyclopropyl-1H-pyrazol-3-ylamino)pyrrolo[1,2-f][1,2,4]triazin-2-yl)cyclopentanecarboxylate

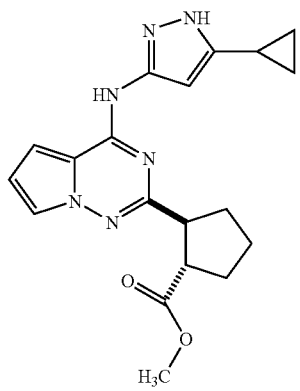

trans-Methyl 2-(4-oxo-3,4-dihydropyrrolo[1,2-f][1,2,4]triazin-2-yl)cyclopentanecarboxylate hydrochloride (450 mg, 1.51 mmol) was dissolved in POCl$_3$ (10 mL, 107 mmol) and heated to 85° C. for 1.5 h, then at 100° C. for an additional 4.5 h. The reaction was cooled to rt and concentrated in vacuo, co-evaporating with toluene several times. NMP (6 mL) was added to the residue, and the reaction was heated to 80° C. before a solution of 5-cyclopropyl-1H-pyrazol-3-amine (922 mg, 7.49 mmol) dissolved in NMP (6 mL) was slowly injected. The reaction was stirred overnight at 80° C., then cooled to rt. EtOAc (250 mL) was added, and the reaction was washed with water (2×150 mL) and brine (150 mL). The organic layer was dried (MgSO$_4$), filtered, and concentrated in vacuo. The compound was purified by silica gel flash chromatography (0-40% 90:10:1 [CH$_2$Cl$_2$/MeOH/conc NH$_4$OH]/CH$_2$Cl$_2$), followed by trituration with 1:1 CH$_2$Cl$_2$/Hex to give 17/18D (260 mg, 50%). 17/18D had an analytical HPLC retention time=2.15 min (Waters XBridge 4.6×50 mm, 5-95% aqueous acetonitrile over 5 min containing 10 mM ammonium acetate) and a LC/MS M$^+$+1=367.

(1R,2R)-2-(4-(5-Cyclopropyl-1H-pyrazol-3-ylamino)pyrrolo[1,2-f][1,2,4]-triazin-2-yl)-N-(6-fluoropyridin-3-yl)cyclopentanecarboxamide and (1S,2S)-2-(4-(5-Cyclopropyl-1H-pyrazol-3-ylamino)pyrrolo[1,2-f][1,2,4]triazin-2-yl)-N-(6-fluoropyridin-3-yl)cyclopentanecarboxamide 6-Fluoropyridin-3-amine (230 mg, 2.05 mmol) was dissolved in THF (8 mL). Methyl magnesiumbromide (3.0 M in ether, 682 μL, 2.05 mmol) was added. After stirring for several min, trans-methyl 2-(4-(5-cyclopropyl-1H-pyrazol-3-ylamino)pyrrolo[1,2-f][1,2,4]triazin-2-yl)cyclopentanecarboxylate (150 mg, 0.409 mmol) was added. The reaction stirred overnight at rt, then water (100 mL) was added. The reaction mixture was extracted with EtOAc (2×75 mL), and the combined organic layers were washed with water (2×100 mL) and brine (100 mL), then dried (MgSO$_4$), filtered, and concentrated in vacuo. The compound was purified by trituration in 1:1 CH$_2$Cl$_2$/Hex to give the racemic compound (134 mg, 73%). The racemate was separated into its enantiomers by chiral preparative HPLC. (The separated enantiomers were not given absolute stereochemical assignments.) Enantiomer A had an analytical HPLC retention time=2.330 min (Phenomenex Luna 3.0×50 mm, 10-90% aqueous MeOH over 5 min containing 0.1% TFA) and a LC/MS M$^+$+1=447. Enantiomer B had an analytical HPLC retention time=2.327 min (Phenomenex Luna 3.0×50 mm, 10-90% aqueous MeOH over 5 min containing 0.1% TFA) and a LC/MS M$^+$+1=447.

Example 19

2-(4-(5-Cyclopropyl-1H-pyrazol-3-ylamino)pyrrolo[1,2-f][1,2,4]triazin-2-yl)-N-(6-fluoropyridin-3-yl)cyclopent-1-enecarboxamide

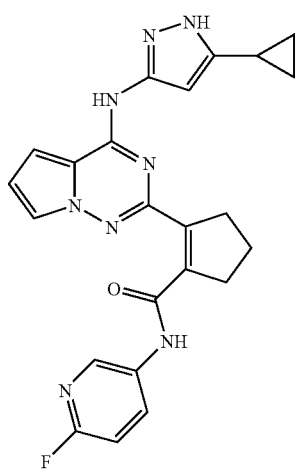

19A. 2-(2-Carbamoyl-1H-pyrrol-1-ylcarbamoyl)cyclopent-1-enecarboxylic acid

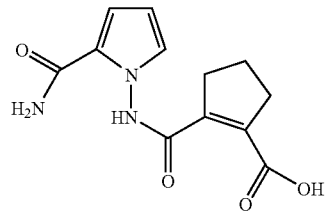

1-Amino-1H-pyrrole-2-carboxamide (91 mg, 0.724 mmol) was dissolved in THF (3 mL), then 1-cyclopentene-1,2-dicarboxylic anhydride (100 mg, 0.724 mmol) was added. The reaction was stirred at rt for 30 min, then 0.5 M HCl (10 mL) was added. The precipitated product was filtered, rinsing with more 0.5 M HCl. The solids were dried to give 19A (177 mg, 92%). 19A had an analytical HPLC retention time=1.597 min (Phenomenex Luna 4.6×50 mm, 10-90% aqueous MeOH over 5 min containing 0.1% TFA) and a LC/MS M$^+$+1=264.

19B. 2-(4-Oxo-3,4-dihydropyrrolo[1,2-f][1,2,4]triazin-2-yl)cyclopent-1-enecarboxylic acid

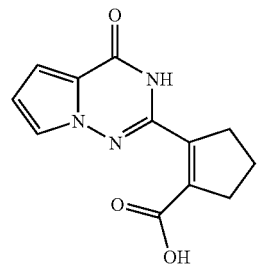

2-(2-Carbamoyl-1H-pyrrol-1-ylcarbamoyl)cyclopent-1-enecarboxylic acid (1.15 g, 4.37 mmol) was dissolved in EtOH (22 mL). 1 M KOH (21.8 mL, 21.8 mmol) was added, and the reaction was heated to reflux for 11 h. Upon cooling to rt, the reaction was diluted with water (75 mL) and adjusted to pH 2 with 1 M HCl. A precipitate formed which was removed by filtration to give 19B (800 mg, 75%). 19B had an analytical HPLC retention time=1.73 min (Waters XBridge 4.6×50 mm, 5-95% aqueous acetonitrile over 5 min containing 10 mM ammonium acetate) and a LC/MS M$^+$+1=246.

19C. Methyl 2-(4-oxo-3,4-dihydropyrrolo[1,2-f][1,2,4]triazin-2-yl)cyclopent-1-enecarboxylate

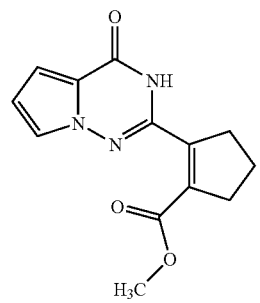

A mixture of 2-(4-oxo-3,4-dihydropyrrolo[1,2-f][1,2,4]triazin-2-yl)cyclopent-1-enecarboxylic acid (950 mg, 3.87 mmol) and sodium acetate (651 mg, 7.75 mmol) was dissolved in DMF (19 mL). Methyl iodide (241 μL, 3.87 mmol) dissolved in DMF (9.5 mL) was injected, followed after stirring 5 h by more methyl iodide (241 µL, 3.87 mmol) dissolved in DMF. The reaction was stirred overnight at rt, then EtOAc (200 mL) was added. The reaction was washed with water (2×200 mL), 1 M NaOH (100 mL), water (200 mL), and brine (200 mL). The 1 M NaOH extracts were acidified to pH 3 with aqueous HCl, then extracted with EtOAc (150 mL). The organic layer was washed with brine (150 mL), then dried (MgSO$_4$), filtered, and concentrated in vacuo. The compound was purified by silica gel flash chromatography (0-10% MeOH/CH$_2$Cl$_2$) to give slightly impure 19C (547 mg, 90%). 19C had an analytical HPLC retention time=2.07 min (Waters XBridge 4.6×50 mm, 5-95% aqueous acetonitrile over 5 min containing 10 mM ammonium acetate) and a LC/MS M$^+$+1=260.

19D. Methyl 2-(4-(5-cyclopropyl-1H-pyrazol-3-ylamino)pyrrolo[1,2-f][1,2,4]triazin-2-yl)cyclopent-1-enecarboxylate

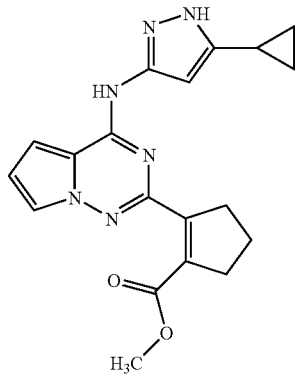

Methyl 2-(4-oxo-3,4-dihydropyrrolo[1,2-f][1,2,4]triazin-2-yl)cyclopent-1-enecarboxylate (450 mg, 1.74 mmol) was dissolved in POCl$_3$ (10 mL, 107 mmol) and heated to 80° C. for 1.5 h. The excess POCl$_3$ was removed in vacuo and co-evaporated several times with toluene. The residue was dissolved in NMP (10 mL) and heated to 80° C. A solution of 5-cyclopropyl-1H-pyrazol-3-amine (855 mg, 6.94 mmol) dissolved in NMP (7 mL) was slowly injected, and the reaction was stirred overnight at 80° C. Upon cooling to rt, the reaction was diluted with EtOAc (200 mL), then washed with water (3×100 mL) and brine (100 mL). The organic layer was dried (MgSO$_4$), filtered, and concentrated in vacuo. The compound was purified by silica gel flash chromatography (0-70% 90:10:1 [CH$_2$Cl$_2$/MeOH/conc NH$_4$OH]/CH$_2$Cl$_2$) to give slightly impure 19E (526 mg, ~80%). 19E had an analytical HPLC retention time=2.845 min (Phenomenex Luna 4.6×50 mm, 10-90% aqueous MeOH over 5 min containing 0.1% TFA) and a LC/MS M$^+$+1=365.

2-(4-(5-Cyclopropyl-1H-pyrazol-3-ylamino)pyrrolo[1,2-f][1,2,4]triazin-2-yl)-N-(6-fluoropyridin-3-yl)cyclopent-1-enecarboxamide 6-Fluoropyridin-3-amine (231 mg, 2.06 mmol) was dissolved in THF (15 mL). Methyl magnesium bromide (3.0 M in ether; 686 µL, 2.06 mmol) was added. After stirring several min, methyl 2-(4-(5-cyclopropyl-1H-pyrazol-3-ylamino)pyrrolo[1,2-f][1,2,4]triazin-2-yl)cyclopent-1-enecarboxylate (150 mg, 0.412 mmol) was added. The reaction was stirred at rt overnight, then EtOAc (100 mL) and water (100 mL) were added. The mixture was filtered through diatomaceous earth, and the layers were separated. The organic layer was washed with water (100 mL) and brine (100 mL), then dried (MgSO$_4$), filtered, and concentrated in vacuo. The compound was purified by preparative HPLC to give the title compound (87 mg, 47%), which had an analytical HPLC retention time=3.068 min (Phenomenex Luna 3.0×50 mm, 10-90% aqueous MeOH over 5 min containing 0.1% TFA) and a LC/MS M$^+$+1=445.

Example 20

2-(4-(5-Cyclopropyl-1H-pyrazol-3-ylamino)pyrrolo[1,2-f][1,2,4]triazin-2-yl)-N-(pyrazin-2-yl)cyclopent-1-enecarboxamide

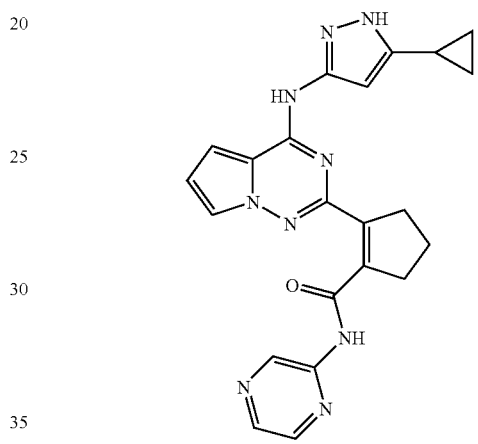

The compound was produced analogously to Example 19 with aminopyrazine (131 mg, 1.37 mmol) and methyl 2-(4-(5-cyclopropyl-1H-pyrazol-3-ylamino)pyrrolo[1,2-f][1,2,4]triazin-2-yl)cyclopent-1-enecarboxylate (100 mg, 0.274 mmol) to give the title compound (52 mg, 44%), which had an analytical HPLC retention time=2.08 min (Waters XBridge 4.6×50 mm, 5-95% aqueous acetonitrile over 5 min containing 10 mM ammonium acetate) and a LC/MS M$^+$+1=428.

Example 21

N-((4-(5-Cyclopropyl-1H-pyrazol-3-ylamino)pyrrolo[1,2-f][1,2,4]triazin-2-yl)methyl)pyrazine-2-carboxamide

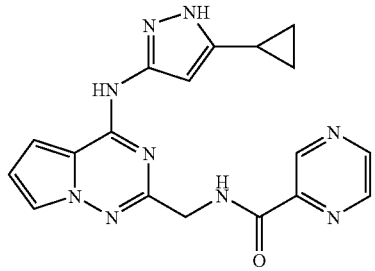

21A. tert-Butyl 2-(2-carbamoyl-1H-pyrrol-1-ylamino)-2-oxoethylcarbamate

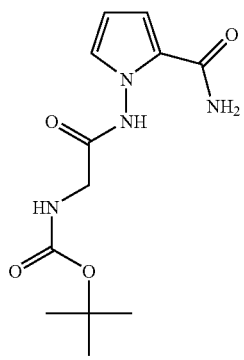

1-Amino-1H-pyrrole-2-carboxamide (5.00 g, 40.0 mmol) and 2-(tert-butoxycarbonylamino)acetic acid (7.70 g, 44.0 mmol) were combined and dissolved in THF (250 mL). To this solution was added EDC (8.43 g, 44.0 mmol). The reaction was stirred at room temperature for 16 h, after which the reaction was concentrated in vacuo. The residue was partitioned between EtOAc (250 mL) and water (200 mL). The layers were separated, and the aqueous layer was extracted with EtOAc (150 mL). The combined organics were dried (MgSO$_4$) and filtered. The filtrate was treated with activated charcoal and filtered over Celite. The filtrate was concentrated in vacuo to remove most of the solvent, then diluted with hexanes to ~1 L. A solid was filtered off and dried to give 21A (8.73 g). The aqueous layer was extracted again with EtOAc (2×100 mL). A second crop was obtained similarly to above to give 465 mg, for a total yield of 9.20 g (82%). 21A had an analytical HPLC retention time=1.75 min (Phenomonex-Luna (4.6×50 mm S10); 10-90% MeOH/H2O (0.1% TFA) over 4 min; flow=4 mL/min) and a LC/MS M$^+$-Boc+1=183.

21B. tert-Butyl (4-oxo-3,4-dihydropyrrolo[1,2-f][1,2,4]triazin-2-yl)methylcarbamate

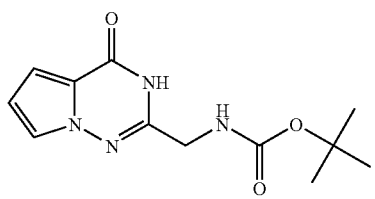

Ethanol (142 mL) was added to tert-butyl 2-(2-carbamoyl-1H-pyrrol-1-ylamino)-2-oxoethylcarbamate (8.00 g, 28.3 mmol), then was added KOH (1.590 g, 28.3 mmol) dissolved in water (142 mL). The reaction was heated to 100° C. for 5 h, then at room temperature for 11 h. The reaction mixture was diluted with water (200 mL) and adjusted to pH 7 with 1.0 N HCl. A precipitate was filtered off and dried at 80° C. under high vacuum to afford 21B (6.44 g, 86%). 21B had an analytical HPLC retention time=1.86 min (Waters XBridge (4.6×50 mm); 5-95% MeCN/H2O (10 mM ammonium acetate) over 5 min; flow=4 mL/min) and a LC/MS M$^+$+1=265.

21C. 2-(Aminomethyl)pyrrolo[1,2-f][1,2,4]triazin-4(3H)-one dihydrochloride

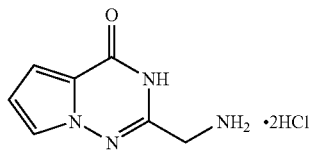

1,4-Dioxane (60 mL) was added to tert-butyl (4-oxo-3,4-dihydropyrrolo[1,2-f][1,2,4]triazin-2-yl)methylcarbamate (6.32 g, 23.91 mmol), to which was added HCl (4.0 M in dioxane, 40 mL, 160 mmol). The reaction was stirred at room temperature for 2.75 h, then an additional amount of HCl (4.0 M in dioxane, 65 mL, 260 mmol) was added. The reaction was stirred at room temperature for 16 h, then diluted with ether (600 mL). A precipitate was filtered off and dried to give 21C (5.87 g, >100%). 21C had an analytical HPLC retention time=0.330 min (Phenomonex-Luna (4.6×50 mm S10); 10-90% MeOH/H2O (0.1% TFA) over 4 min; flow=4 mL/min) and a LC/MS M$^+$+1=165.

21D. 2-((4-Oxo-3,4-dihydropyrrolo[1,2-f][1,2,4]-triazin-2-yl)methyl)isoindoline-1,3-dione

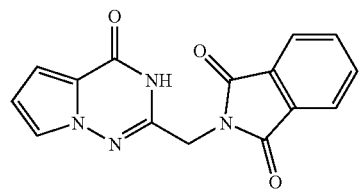

2-(Aminomethyl)pyrrolo[1,2-f][1,2,4]triazin-4(3H)-one dihydrochloride (5.85 g, 24.67 mmol) was dissolved in DMF (150 mL), then DIPEA (8.62 mL, 49.3 mmol) was added, followed by phthalic anhydride (7.31 g, 49.3 mmol). The reaction was heated to 75° C. for 4 h, after which the reaction was removed from heat and immediately poured into water (1.2 L). The suspension was filtered, and the filter cake was rinsed with MeOH and dried to afford 21D (7.09 g, 98%). 21D had an analytical HPLC retention time=2.825 min (Phenomonex-Luna (4.6×50 mm S10); 10-90% MeOH/H2O (0.1% TFA) over 4 min; flow=4 mL/min) and a LC/MS M$^+$+1=295.

21E. 2-((4-Chloropyrrolo[1,2-f][1,2,4]triazin-2-yl)methyl)isoindoline-1,3-dione

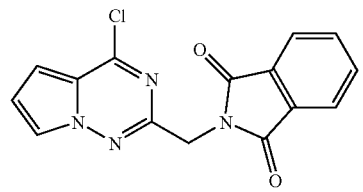

POCl$_3$ (100 mL, 1073 mmol) was added to 2-((4-oxo-3,4-dihydropyrrolo[1,2-f][1,2,4]triazin-2-yl)methyl)isoindoline-1,3-dione (6.00 g, 20.39 mmol) and the mixture was heated to 100° C. for 7 h. Most of the POCl₃ was removed in vacuo, and the reaction was diluted with hexanes (300 mL). After vigorous stirring, the supernatant was decanted, and the residue was again stirred with hexanes (300 mL). After decanting the supernatant, DCM (300 mL) was added, and after vigorous stirring, the solids were filtered off. The filtrate was treated with activated charcoal and filtered over Celite. The filtrate was concentrated in vacuo, then diluted with hexanes. A solid was filtered and dried. Both of the above solids were stirred vigorously with 100 mL water, then filtered and dried to give a combined yield of 21E (4.83 g, 76%). 21E had an analytical HPLC retention time=3.563 min (Phenomonex-Luna (4.6× 50 mm S10); 10-90% MeOH/H2O (0.1% TFA) over 4 min; flow=4 mL/min) and a LC/MS M⁺+1=313 & 315.

21F. 2-((4-(5-Cyclopropyl-1H-pyrazol-3-ylamino)pyrrolo[1,2-f][1,2,4]triazin-2-yl)methyl)isoindoline-1,3-dione

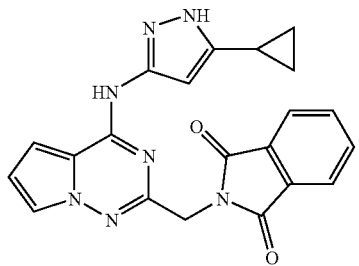

2-((4-Chloropyrrolo[1,2-f][1,2,4]triazin-2-yl)methyl)isoindoline-1,3-dione (4.43 g, 14.17 mmol) was suspended in NMP (50 mL), then DIPEA (4.95 mL, 28.3 mmol) was added. The mixture was heated to 80° C., to which was slowly added via syringe a solution of 5-cyclopropyl-1H-pyrazol-3-amine (3.49 g, 28.3 mmol) in NMP (20 mL). The reaction was stirred at 80° C. for 2 h, then cooled to room temperature. The reaction was diluted with EtOAc (700 mL) and washed with water (3×500 mL) and brine (2×250 mL). The organics were dried (MgSO₄), filtered, and concentrated in vacuo. The residue was dissolved in a minimum of EtOAc and diluted with hexanes, and the precipitate was filtered and dried. The solids were triturated twice with 20% EtOAc/Hex, once with 20% DCM/Hex, and finally in 50% DCM/Hex to give 21F (3.35 g, 59%). 21F had an analytical HPLC retention time=3.368 min (Phenomonex-Luna (4.6×50 mm S10); 10-90% MeOH/H2O (0.1% TFA) over 4 min; flow=4 mL/min) and a LC/MS M⁺+1=400.

21G. 2-(Aminomethyl)-N-(5-cyclopropyl-1H-pyrazol-3-yl)pyrrolo[1,2-f][1,2,4]-triazin-4-amine

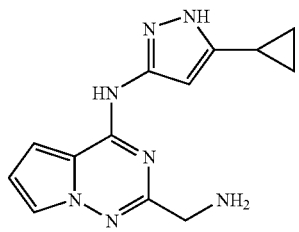

2-((4-(5-Cyclopropyl-1H-pyrazol-3-ylamino)pyrrolo[1,2-f][1,2,4]triazin-2-yl)methyl)isoindoline-1,3-dione (3.30 g, 8.26 mmol) was suspended in EtOH (83 mL), then hydrazine monohydrate (4.01 mL, 83 mmol) was added. The reaction was stirred vigorously at room temperature for 3 h. Water (200 mL) was added, and the solution was extracted with EtOAc (250 mL, then 2×150 mL). The combined organics were washed with brine (200 mL), dried (MgSO₄), and filtered. The filtrate was vigorously stirred with activated charcoal, then filtered over Celite, and concentrated in vacuo. The residue was taken up in MeOH and DCM, then concentrated in vacuo. The residue was stirred vigorously with hexanes until the stickiness of the residue had given way to a suspension. A solid was filtered off and dried. The material was redissolved in EtOH (83 mL). Hydrazine monohydrate (4.01 mL, 83 mmol) was added, and the reaction was heated to 40° C. for 16 h. The reaction was cooled to room temperature and concentrated in vacuo. EtOAc (200 mL) and water (200 mL) were added, and the layers were separated. The aqueous layer was extracted with EtOAc (3×100 mL), and the combined organics were dried (MgSO₄), filtered, and concentrated in vacuo to remove most of the solvent. The concentrate was diluted with hexanes to precipitate a solid, which was filtered and dried to give 21G (1.27 g, 57%). 21G had an analytical HPLC retention time=1.880 min (Phenomonex-Luna (4.6× 50 mm S10); 10-90% MeOH/H2O (0.1% TFA) over 4 min; flow=4 mL/min) and a LC/MS M⁺+1=270.

N-((4-(5-Cyclopropyl-1H-pyrazol-3-ylamino)pyrrolo[1,2-f][1,2,4]triazin-2-yl)methyl)pyrazine-2-carboxamide 2-(Aminomethyl)-N-(5-cyclopropyl-1H-pyrazol-3-yl)pyrrolo[1,2-f][1,2,4]triazin-4-amine (75 mg, 0.278 mmol) was dissolved in NMP (1.5 mL), then DIPEA (73 μL, 0.418 mmol), pyrazine-2-carboxylic acid (38.0 mg, 0.306 mmol), and HATU (116 mg, 0.306 mmol) were added. The reaction was stirred at room temperature for 2.5 h. The reaction was diluted with water (20 mL) and an off-white precipitate was filtered off and dried, which was purified via a Biotage 25M column (0 to 50% 90:10:1 [DCM/MeOH/NH₄OH]/DCM) to give the title compound (57 mg, 54%), which had an analytical HPLC retention time=2.675 min (Phenomonex-Luna (4.6×50 mm S10); 10-90% MeOH/H2O (0.1% TFA) over 4 min; flow=4 mL/min) and a LC/MS M⁺+1=376.

Example 22

N-((4-(5-Cyclopropyl-1H-pyrazol-3-ylamino)pyrrolo[1,2-f][1,2,4]triazin-2-yl)methyl)-6-fluoronicotinamide

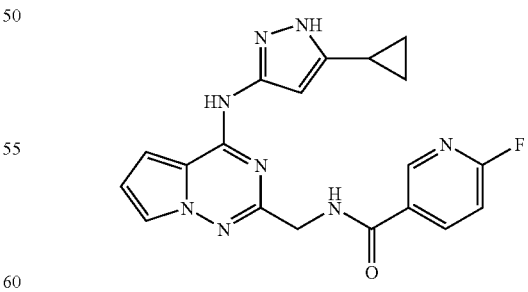

The reaction was performed analogously to Example 21 with 2-(aminomethyl)-N-(5-cyclopropyl-1H-pyrazol-3-yl)pyrrolo[1,2-f][1,2,4]triazin-4-amine (75 mg, 0.278 mmol) and 6-fluoronicotinic acid (41.3 mg, 0.292 mmol) to obtain the title compound (60 mg, 55%), which had an analytical HPLC retention time=2.756 min (Phenomonex-Luna (4.6×

50 mm S10); 10-90% MeOH/H2O (0.1% TFA) over 4 min; flow=4 mL/min) and a LC/MS M++1=393.

Example 23

N-((4-(5-Cyclopropyl-1H-pyrazol-3-ylamino)pyrrolo[1,2-f][1,2,4]triazin-2-yl)methyl)thiazole-2-carboxamide

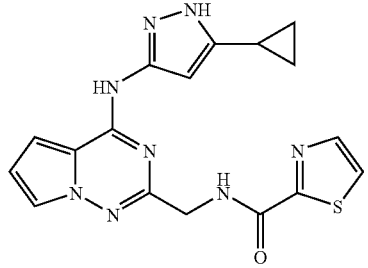

2-(Aminomethyl)-N-(5-cyclopropyl-1H-pyrazol-3-yl)pyrrolo[1,2-f][1,2,4]triazin-4-amine (75 mg, 0.278 mmol) was dissolved in NMP (1.5 mL), then DIPEA (73 µL, 0.418 mmol) was added, followed by thiazole-2-carbonyl chloride (48.0 mg, 0.292 mmol). The solution was stirred at room temperature for 30 min. The reaction was diluted with water (20 mL), and an off-white solid was filtered off and dried. The residue was purified via a Biotage 25M column (0 to 30% 90:10:1 [DCM/MeOH/NH4OH]/DCM) to give the title compound (74 mg, 69%), which had an analytical HPLC retention time=2.482 min (Phenomonex-Luna (4.6×50 mm S10); 10-90% MeOH/H2O (0.1% TFA) over 4 min; flow=4 mL/min) and a LC/MS M++1=381.

Example 24

N-((4-(5-Cyclopropyl-1H-pyrazol-3-ylamino)pyrrolo[1,2-f][1,2,4]triazin-2-yl)methyl)-2-oxoimidazolidine-1-carboxamide

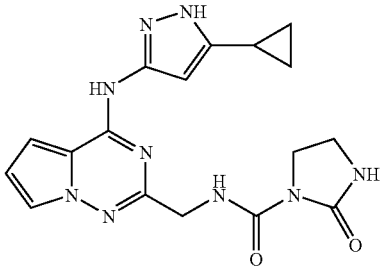

2-(Aminomethyl)-N-(5-cyclopropyl-1H-pyrazol-3-yl)pyrrolo[1,2-f][1,2,4]triazin-4-amine (75 mg, 0.278 mmol) was dissolved in NMP (1.5 mL), then DIPEA (73 mL, 0.418 mmol) was added, followed by 2-oxoimidazolidine-1-carbonyl chloride (41.4 mg, 0.278 mmol). The reaction was stirred at room temperature for 15 min. The reaction was diluted with water (20 mL) and the precipitate was filtered and dried. The residue was purified via a Biotage 25M column (0 to 40% 90:10:1 [DCM/MeOH/NH4OH]/DCM) to give the title compound (49 mg, 46%), which had an analytical HPLC retention time=2.458 min (Phenomonex-Luna (4.6×50 mm S10); 10-90% MeOH/H2O (0.1% TFA) over 4 min; flow=4 mL/min) and a LC/MS M++1=382.

We claim:

1. A compound of formula II

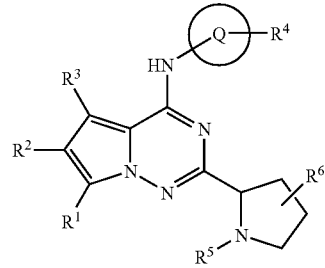

wherein:

Q is pyrazole or imidazole;

$R^1$, $R^2$, and $R^3$ are independently hydrogen, alkyl, substituted alkyl or halogen;

$R^4$ is hydrogen, alkyl, substituted alkyl, hydroxy, alkoxy, halogen, cycloalkyl, or substituted cycloalkyl;

$R^5$ is hydrogen, alkyl, substituted alkyl, alkylidene, substituted alkylidene, haloalkyl, arylalkyl, alkanoyl, substituted alkanoyl, aminoalkyl, substituted aminoalkyl, hydroxyalkyl, amide, substituted amide, carbamate, substituted carbamate, ureido, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, thioalkyl, alkylsulfonyl, alkylsulfinyl, carboxy, alkoxycarbonyl, carbamoyl, alkenyl, substituted alkenyl, alkynyl, substituted alkynyl, aryl, substituted aryl, heteroaryl, substituted heteroaryl, arylheteroaryl, arylalkoxycarbonyl, heteroarylalkyl, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylsulfonyl, arylalkylsulfonyl, alkylsulfonyl, or alkylaminocarbonyl, —COalkyl, —CO substituted alkyl; —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO2 alkyl, —SO2 substituted alkyl; —SO2 aryl, —SO2 substituted aryl, —SO2 heteroaryl, —SO2 substituted heteroaryl, —SO2 heterocyclyl or —SO2 substituted heterocyclyl;

$R^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

2. A compound of formula III

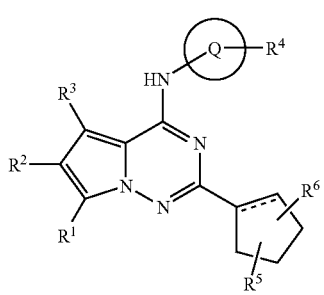

(III)

wherein:
Q is pyrazole or imidazole;
$R^1$, $R^2$, and $R^3$ are independently hydrogen, alkyl, substituted alkyl or halogen;
$R^4$ is hydrogen, alkyl, substituted alkyl, hydroxy, alkoxy, halogen, cycloalkyl, or substituted cycloalkyl;
$R^5$ is hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl, —COalkyl, —CO substituted alkyl, —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO₂ alkyl, —SO₂ substituted alkyl; —SO₂ aryl, —SO₂ substituted aryl, —SO₂ heteroaryl, —SO₂ substituted heteroaryl, —SO₂ heterocyclyl or —SO₂ substituted heterocyclyl;
$R^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;
or a pharmaceutically acceptable salt, tautomer or stereoisomer thereof.

3. A compound of formula IV

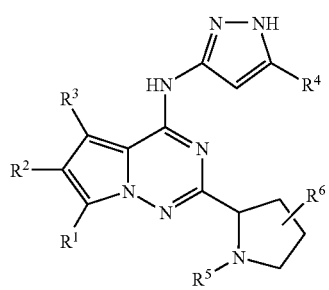

(IV)

wherein:
$R^1$, $R^2$, and $R^3$ are independently hydrogen, alkyl, substituted alkyl or halogen;
$R^4$ is hydrogen, alkyl, substituted alkyl, hydroxy, alkoxy, halogen, cycloalkyl, or substituted cycloalkyl;
$R^5$ is hydrogen, alkyl, substituted alkyl, alkylidene, substituted alkylidene, haloalkyl, arylalkyl, alkanoyl, substituted alkanoyl, aminoalkyl, substituted aminoalkyl, hydroxyalkyl, amide, substituted amide, carbamate, substituted carbamate, ureido, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, thioalkyl, alkylsulfonyl, alkylsulfinyl, carboxy, alkoxycarbonyl, carbamoyl, alkenyl, substituted alkenyl, alkynyl, substituted alkynyl, aryl, substituted aryl, heteroaryl, substituted heteroaryl, arylheteroaryl, arylalkoxycarbonyl, heteroarylalkyl, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylsulfonyl, arylalkylsulfonyl, alkylsulfonyl, or alkylaminocarbonyl,
—COalkyl, —CO substituted alkyl; —COaryl, —CO substituted aryl, —CO heteroaryl, —CO substituted heteroaryl, —CO heterocyclyl, —CO substituted heterocyclyl, —CONHalkyl, —CONH substituted alkyl; —CONH aryl, —CONH substituted aryl, —CONH heteroaryl, —CONH substituted heteroaryl, —CONH heterocyclyl, —CONH substituted heterocyclyl, —SO₂ alkyl, —SO₂ substituted alkyl; —SO₂ aryl, —SO₂ substituted aryl, —SO₂ heteroaryl, —SO₂ substituted heteroaryl, —SO₂ heterocyclyl or —SO₂ substituted heterocyclyl;
$R^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;
or a pharmaceutically acceptable salt, tautomer or stereoisomer thereof.

4. A compound of formula V

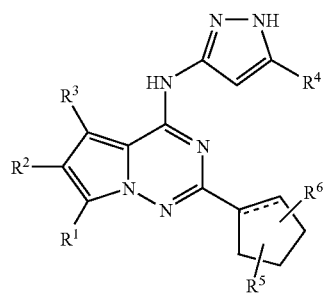

wherein:
- $R^1$, $R^2$, and $R^3$ are independently hydrogen, alkyl, substituted alkyl, or halogen;
- $R^4$ is hydrogen, alkyl, substituted alkyl, hydroxy, alkoxy, halogen, cycloalkyl, or substituted cycloalkyl;
- $R^5$ is hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl, —COalkyl, —CO substituted alkyl, —COaryl, —CO substituted aryl, —CO heteroaryl, —CO substituted heteroaryl, —CO heterocyclyl, —CO substituted heterocyclyl, —CONHalkyl, —CONH substituted alkyl, —CONH aryl, —CONH substituted aryl, —CONH heteroaryl, —CONH substituted heteroaryl, —CONH heterocyclyl, —CONH substituted heterocyclyl, —$SO_2$ alkyl, —$SO_2$ substituted alkyl; —$SO_2$ aryl, —$SO_2$ substituted aryl, —$SO_2$ heteroaryl, —$SO_2$ substituted heteroaryl, —$SO_2$ heterocyclyl or —$SO_2$ substituted heterocyclyl;
- $R^6$ is hydrogen, halogen, cyano, hydroxy, oxo, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl or substituted heteroalkynyl;

or a pharmaceutically acceptable salt, tautomer or stereoisomer thereof.

5. A pharmaceutical composition comprising a pharmaceutically acceptable carrier and one or more compounds of claim 1 or a pharmaceutically acceptable salt or stereoisomer thereof.

6. A pharmaceutical composition comprising a pharmaceutically acceptable carrier and one or more compounds of claim 2 or a pharmaceutically acceptable salt or stereoisomer thereof.

7. A pharmaceutical composition comprising a pharmaceutically acceptable carrier and one or more compounds of claim 3 or a pharmaceutically acceptable salt or stereoisomer thereof.

8. A pharmaceutical composition comprising a pharmaceutically acceptable carrier and one or more compounds of claim 4 or a pharmaceutically acceptable salt or stereoisomer thereof.

9. A method for the treatment of breast cancer, comprising administering to a patient in need thereof a therapeutically effective amount of a compound of claim 1 or a stereoisomer or pharmaceutically acceptable salt thereof.

* * * * *